US006960697B2

(12) United States Patent
O'Young et al.

(10) Patent No.: US 6,960,697 B2
(45) Date of Patent: Nov. 1, 2005

(54) SYSTEM AND METHOD OF PRODUCING BISPHENOL-A (BPA)

(75) Inventors: Drow Lionel O'Young, West Covina, CA (US); Shan Tao Hsieh, San Jose, CA (US); Vaibhav Kelkar, Sunnyvale, CA (US)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/099,227

(22) Filed: Mar. 13, 2002

(65) Prior Publication Data

US 2003/0181768 A1 Sep. 25, 2003

(51) Int. Cl.⁷ .............................................. C07C 39/16
(52) U.S. Cl. ..................................................... 568/728
(58) Field of Search ................................. 568/728, 724

(56) References Cited

U.S. PATENT DOCUMENTS

| | | |
|---|---|---|
| 1,978,949 A | 10/1934 | Kohn et al. |
| 2,191,831 A | 2/1940 | Perkins et al. |
| 2,730,553 A | 1/1956 | Williamson et al. |
| 2,775,620 A | 12/1956 | Williamson et al. |
| 2,791,616 A | 5/1957 | Luten, Jr. et al. |
| 3,164,640 A | 1/1965 | Bostian et al. |
| 3,326,986 A | 6/1967 | Dugan et al. |
| 3,972,950 A | 8/1976 | Kwantes |
| 4,053,522 A | 10/1977 | McClure et al. |
| 4,079,087 A | 3/1978 | Sun |
| 4,141,924 A | 2/1979 | Sun |
| 4,191,843 A | 3/1980 | Kwantes et al. |
| 4,192,955 A * | 3/1980 | Reinitz ....................... 568/724 |
| 4,209,646 A | 6/1980 | Gac et al. |
| 4,294,994 A | 10/1981 | Li |
| 4,308,404 A | 12/1981 | Kwantes et al. |
| 4,308,405 A | 12/1981 | Kwantes |
| 4,354,046 A | 10/1982 | Ladewig et al. |
| 4,369,293 A | 1/1983 | Heydenreich et al. |
| 4,391,997 A | 7/1983 | Mendiratta |
| 4,400,555 A | 8/1983 | Mendiratta |
| 4,443,635 A | 4/1984 | McLaughlin |
| 4,492,807 A | 1/1985 | Aneja |
| 4,514,574 A | 4/1985 | Inoue et al. |
| 4,529,823 A | 7/1985 | Mendiratta |
| 4,533,764 A | 8/1985 | Chang et al. |
| 4,590,303 A | 5/1986 | Mendiratta |
| 4,638,102 A | 1/1987 | Little |
| 4,740,635 A | 4/1988 | Gomes de Matos et al. |
| 4,798,654 A | 1/1989 | Iimuro et al. |
| 4,820,740 A | 4/1989 | Li |
| 4,847,433 A | 7/1989 | Kissinger |
| 4,859,803 A | 8/1989 | Shaw |
| 4,861,919 A | 8/1989 | Robbins et al. |
| 4,906,789 A | 3/1990 | Grzywa et al. |
| 4,927,973 A | 5/1990 | Dong et al. |
| 4,927,978 A | 5/1990 | Buechele et al. |
| 5,008,470 A | 4/1991 | Powell et al. |
| 5,015,784 A | 5/1991 | Rudolph et al. |
| 5,059,721 A | 10/1991 | Powell et al. |
| 5,075,511 A | 12/1991 | Li |
| 5,105,026 A | 4/1992 | Powell et al. |
| 5,198,591 A | 3/1993 | Kiedik et al. |
| 5,210,329 A | 5/1993 | Gomes de Matos et al. |
| 5,269,887 A | 12/1993 | Jakob et al. |
| 5,288,926 A | 2/1994 | Patrascu et al. |
| 5,300,700 A | 4/1994 | Malamet et al. |
| 5,302,774 A | 4/1994 | Berg et al. |
| 5,315,042 A | 5/1994 | Cipullo et al. |
| 5,324,867 A | 6/1994 | Asaoka et al. |
| 5,345,000 A | 9/1994 | Moriya et al. |
| 5,368,827 A | 11/1994 | Moriya et al. |
| 5,371,304 A | 12/1994 | Asaoka et al. |
| 5,382,712 A | 1/1995 | Asaoka et al. |
| 5,395,857 A | 3/1995 | Berg et al. |
| 5,399,784 A | 3/1995 | Asaoka et al. |
| 5,414,151 A | 5/1995 | Pressman et al. |
| 5,434,316 A | 7/1995 | Kissinger |
| 5,475,152 A | 12/1995 | Kissinger et al. |
| 5,502,016 A | 3/1996 | Kiedik et al. |
| 5,512,700 A | 4/1996 | Patrascu et al. |
| 5,545,764 A | 8/1996 | Berg et al. |
| 5,629,457 A | 5/1997 | Zhang et al. |
| 5,648,561 A | 7/1997 | Tan et al. |
| 5,696,295 A | 12/1997 | Wulff et al. |
| 5,698,600 A | 12/1997 | Wulff et al. |
| 5,723,688 A | 3/1998 | Patrascu et al. |
| 5,756,860 A | 5/1998 | Meurer et al. |
| 5,777,180 A | 7/1998 | June et al. |
| 5,780,690 A | 7/1998 | Berg et al. |
| 5,783,733 A | 7/1998 | Kissinger |
| 5,785,823 A | 7/1998 | Meurer et al. |
| 5,786,522 A | 7/1998 | Cipullo |
| 5,914,431 A | 6/1999 | Fennhoff |
| 5,919,990 A | 7/1999 | Likibi |
| 6,191,316 B1 | 2/2001 | Fennhoff et al. |
| 2003/0181768 A1 | 9/2003 | O'Young et al. |

* cited by examiner

Primary Examiner—Michael L. Shippen
(74) Attorney, Agent, or Firm—Dorsey & Whtiney LLP

(57) ABSTRACT

A system and method for producing bisphenol-A (BPA) is provided. In particular, the present invention provides a system and method of producing bisphenol-A wherein the phase equilibrium behavior of a feed solution to a crystallizer is selectively controlled and adjusted to provide desired results. This provides a powerful tool, whereby certain operating conditions or variables of the bisphenol-A process can be selectively adjusted to generate desired phase equilibrium behavior. In general, bisphenol-A is produced from a reaction of phenol and acetone, forming a product solution including phenol, bisphenol-A, isomers of bisphenol-A, unreacted reactants and by-products. A solvent is provided in the product solution and the amount and composition of solvent in the product solution are selectively controlled to adjust the composition of the product solution fed to a crystallizer such that either crystalline bisphenol-A, or an adduct of bisphenol-A and phenol is crystallized from the product solution. Thus, a solvent is used to selectively control the phase behavior of the system. The solvent is a pseudo component and may be comprised of a single component or may be comprised of a solvent mixture of two or more solvents each exhibiting certain phase behavior in the system.

21 Claims, 13 Drawing Sheets

SYSTEM AND METHOD OF PRODUCING BISPHENOL-A (BPA)

FIELD OF THE INVENTION

The present invention relates in general to a system and method of producing bisphenol-A (BPA). More specifically, the present invention provides a system and method for producing bisphenol-A wherein certain phase equilibrium conditions are selectively controlled.

BACKGROUND OF THE INVENTION

The production of bisphenols such as bisphenol-A (BPA) is an important process as bisphenol-A is used in a variety of chemical industries. For example bisphenols are used to produce polymers such as epoxy resins and polycarbonates. In one application, bisphenol-A is reacted with phosgene to produce commercial polycarbonate resins. High quality polycarbonates, such as those used as optical media in the electronics and disk drive industry, requires highly pure bisphenol-A as a reactant. Consequently, much effort has been focused on developing processes to produce bisphenol-A of high purity.

In general, bisphenol-A is produced by a known liquid-phase condensation reaction of phenol with acetone in the presence of an acid catalyst. The reaction product typically includes bisphenol-A, unreacted reactants, by-products of the reaction most notably water, and impurities such as isomers, analogs and homologs. A variety of processes are used to purify and recover bisphenol-A crystals from the reaction product. Purification and recovery of the bisphenol-A typically represents about one half or more of the total capital investment of the system, and known techniques are often very costly.

Phenol, water and acetone are typically removed, often by distillation, prior to recovery of the bisphenol product by crystallization. U.S. Pat. No. 5,783,733 describes one prior art method of producing bisphenol-A wherein phenol and a ketone are reacted in the presence of an ion exchange resin catalyst to produce a reaction product stream including bisphenol-A. Prior to crystallization excess phenol, water and acetone are removed from the product stream. Crystallization, in this case melt crystallization, is used to purify the crude bisphenol, specifically multiple stage fractional melt crystallization with successive steps of crystallization, partial melting (sweating) and total melting is used. Such phenol removal and melt crystallization techniques are very costly in terms of capital equipment and energy consumption.

In another prior art technique, the reaction product stream is fed directly to a crystallizer where a slurry is formed consisting of a liquid phase, and a solid crystal phase of an equal-molar adduct of bisphenol-A and phenol. The adduct crystals are separated from the liquid (referred to as mother liquor) and phenol is removed from the adduct in a series of phenol removal or dephenolation steps. This prior art method is described for example in U.S. Statutory Invention Registration US H1943. The steps to remove phenol from the adduct, such as distillation or nitrogen desorption, are quite costly and add to the complexity of the system. Finally, multiple stage fractional melt crystallization is preformed to produce the product bisphenol-A.

Many variations to the bisphenol-A process have been proposed by the prior art. Another example is described in U.S. Pat. No. 5,723,688, which provides a method of preparing an adduct of bisphenol with a phenolic compound wherein distillation of the reaction product stream prior to crystallization is omitted. Specifically, U.S. Pat. No. 5,723,688 describes a method of reacting a carbonyl compound with a stoichiometric excess of a phenolic compound in the presence of an acidic cation exchange resin to produce a product mixture containing bisphenol, unreacted phenolic compound, unreacted carbonyl compound and water. The product mixture is then crystalized to form an adduct of bisphenol with the phenolic compound. Once formed the adduct is preferably washed with a phenolic compound which undergoes costly treatment such that at least a portion of the phenolic compound has been purified by means of an acidic cation exchange resin and a basic cation exchange resin. To recover bisphenol-A from the adduct, dephenolation steps are employed where the solid adduct is melted and the phenolic compound is recovered by distillation.

While advances have been made in the production of bisphenol-A, further improvements are needed. The aforementioned prior art methods require costly phenol removal steps and/or phenol purification steps, and costly multiple steps to purify the adduct and/or bisphenol. Further, as the purity requirements for bisphenol-A crystals become more rigorous, the complexity and costs of producing bisphenol-A increase. Accordingly, improved methods for producing bisphenol-A are needed.

SUMMARY OF THE INVENTION

Accordingly, the present invention provides a system and method for producing bisphenol-A. In particular, the present invention is an improved system and method which provides for selectively controlling the process to produce either a solid adduct of bisphenol-A and phenol or substantially pure bisphenol-A crystals.

Of significant advantage, and contrary to the teachings of the prior art, the system and method of the present invention provides for the direct crystallization of bisphenol-A thereby omitting, or significantly reducing, the costly phenol removal steps, especially in the low phenol concentration range. Further, the present invention provides for selectively tailoring the process to produce solid adduct or bisphenol-A crystals, thereby providing flexibility in operation and/or design of the systems heretofore unavailable by the prior art.

The inventors have discovered a system and method of producing bisphenol-A wherein the phase equilibrium behavior of a feed solution to a crystallizer is selectively controlled and adjusted to provide desired results. This provides a powerful tool, whereby certain operating conditions or variables of the bisphenol-A process can be selectively adjusted to generate desired phase equilibrium behavior.

A system and method is described wherein the phase equilibrium of a system comprised of phenol, bisphenol-A and solvent is selectively controlled to recover bisphenol-A (BPA). Among the advantages this minimizes vaporization of phenol and reduces the number of process equipment and steps required to produce bisphenol-A, thereby reducing capital and energy costs. It should be understood by those of ordinary skill in the art that the system may include other components or solutes; however, for purposes on the present invention the system is concerned only with the three primary components—phenol, bisphenol-A and solvent—and thus the phase equilibrium of the system is characterized as a ternary system. More specifically, bisphenol-A is produced from a reaction of phenol and acetone, forming a product solution including phenol, bisphenol-A, isomers of bisphenol-A, unreacted reactants and by-products. A solvent is provided in the product solution and the amount of solvent in the product solution is selectively controlled to adjust the composition of the product solution fed to a crystallizer such that either crystalline bisphenol-A, or an adduct of bisphenol-A and phenol is crystallized from the product solution. Thus, a solvent is used to selectively control the phase behavior of the system. The solvent is a pseudo component and may be comprised of a single component or may be comprised of a solvent mixture of two or more solvents. When a mixture is used at least a first solvent component is selected which exhibits a first phase behavior, and at least a second solvent component is selected to exhibit a second phase behavior. Alternatively, the first and second solvent may exhibit similar phase behaviors. The ratio of the at least first to second solvent components in the solvent mixture is selected to provide a final desired phase behavior. The first and second solvents may be single components, or may in fact be a mixture of components that exhibit the desired phase behavior. The boiling temperature of each solvent is selected such that the mixture will provide desirable operating conditions in terms of solubility and temperature in the crystallizer unit.

In another aspect, the present invention provides a method of producing bisphenol-A, comprising the steps of: reacting phenol and acetone in the presence of a catalyst to form a product solution including bisphenol-A, phenol; providing a solvent in the product solution; and adjusting composition of at least the solvent in the product solution fed to a crystallizer to selectively control the formation of either substantially pure solid bisphenol-A or an adduct of bisphenol-A and phenol from said product solution during crystallization.

In yet another aspect, the present invention provides a method of separating solid bisphenol-A from a solution, comprising the steps of:

providing the solution comprised of at least bisphenol-A, phenol and a solvent component, and where the bisphenol-A and phenol may form an adduct, where the solvent component is comprised of two or more solvents;

and where the bisphenol-A, phenol and solvent components exhibit a phase equilibrium relationship which can be represented by a ternary phase diagram and where the bisphenol-A, phenol and solvent components are in phase equilibrium and exhibit phase behavior which establishes at least two regions in the phase diagram, an adduct region and a pure solid bisphenol-A region;

manipulating the relative size of the adduct and pure solid bisphenol-A regions by adjusting the concentration ratio of the two or more solvents;

adjusting the composition of the solution prior to crystallization to place the solution concentration at a location selectively within either the adduct or the pure solid bisphenol-A region; and crystallizing the solution to form solid bisphenol-A, as either adduct or pure solid bisphenol-A, as selected.

BRIEF DESCRIPTION OF THE DRAWINGS

Other objects and advantages of the present invention become apparent upon reading of the detailed description of the invention provided below and upon reference to the drawings in which.

DETAILED DESCRIPTION OF THE INVENTION

The inventors have discovered a system and method of producing bisphenol wherein the phase equilibrium behavior of the feed stream or feed solution to a crystallizer is selectively controlled to provide selected results for process operation. The invention provides for manipulation and selective control of the phase equilibrium of bisphenol-A, phenol and solvent. It should be understood by those of ordinary skill in the art that the system may include other components or solutes such as impurities, unreacted reactants, isomers and the like; however, for purposes on the present invention we are concerned only with the three primary components in the solution—phenol, bisphenol-A and solvent—where the solvent is a pseudo-component representing a single component solvent or a multi-component solvent, and thus the system is characterized as a ternary phase equilibrium system.

Figure 1:
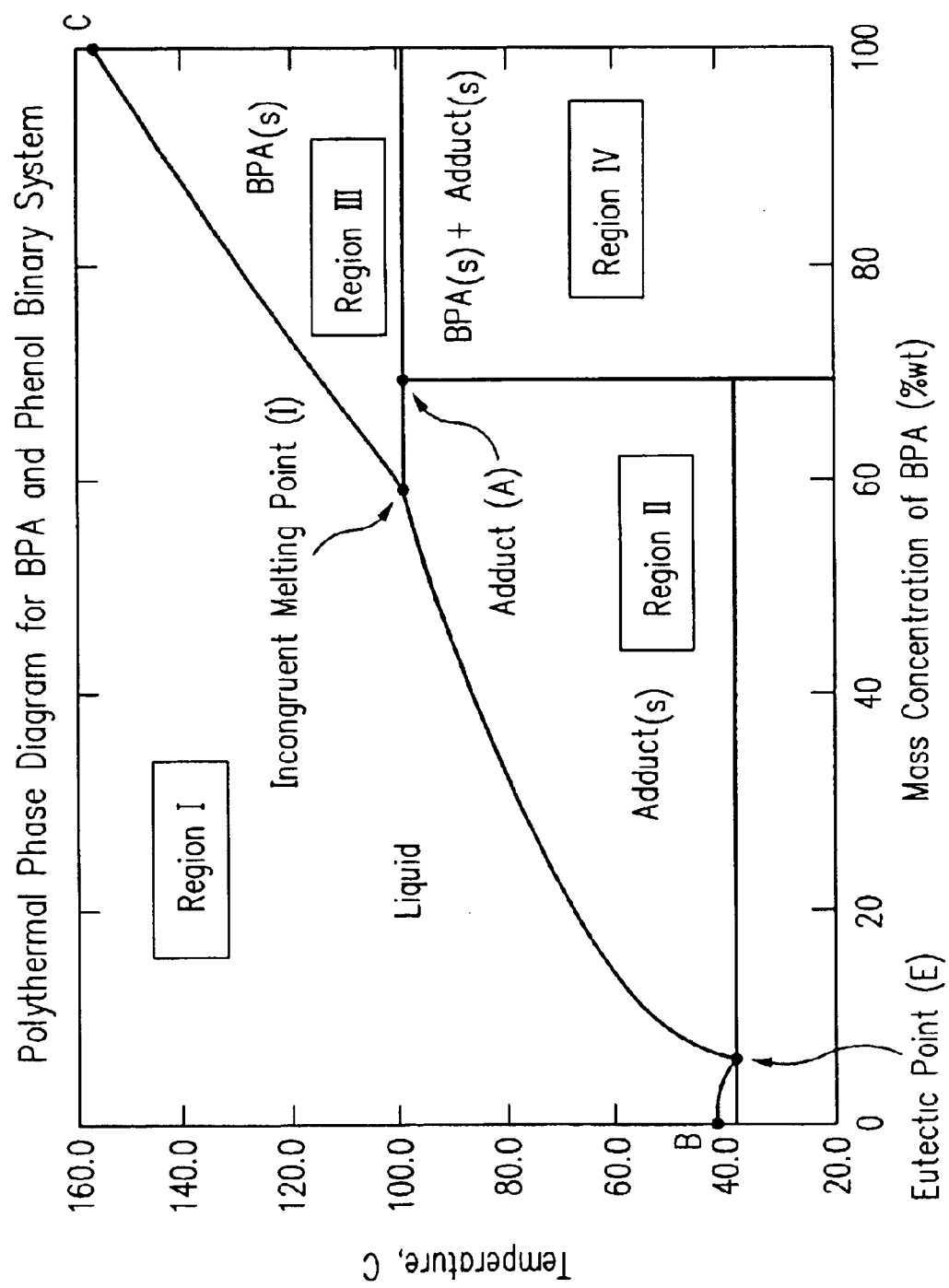
FIG. 1 is a polythermal phase equilibrium diagram for a binary system of bisphenol-A and phenol as found in the prior art.

In the prior art, the phase equilibrium of the bisphenol system for crystallization is typically considered as a binary system comprised of bisphenol-A and phenol as shown in FIG. 1. Since pressure has little effect on the equilibria between solids and liquids, the phase changes for a binary system can be represented on a temperature-concentration diagram. A plurality of phase regions are shown. In Region I, bounded by the liquidus transition line BEIC, both components (i.e. bisphenol-A and phenol) are in the liquid phase. A eutectic exists at point E. An incongruent melting point exists at point I. Solid adduct is formed as shown in Region II. The solid adduct is comprised of an equal-molar composition of bisphenol-A and phenol. Solid bisphenol-A is formed in Region III. In Region IV both solid adduct and solid bisphenol-A phases exist.

The scope of the prior art for the separation of phenol from bisphenol-A can be described by use of the binary phase diagrams illustrated in FIG. 1. To describe the phase behavior of a three-component system, a three-dimensional diagram (3D) is required to illustrate the relationship between temperature and concentration. Normally, the Z axis is for temperature while the X-Y plane is for the concentration. By use of this three-dimensional diagram, the saturation of each component can be described. However, it is very difficult to read the scale of 3D diagram and hence, it is not convenient to perform a conceptual design from the 3D diagram.

It is a common practice in conceptual design stage to reduce a 3D diagram to a 2D diagram, or a 2D diagram to a 1D diagram, for easy visualization and process design purpose. After this reduction, the temperature is projected into the two-dimensional diagram or one-dimensional diagram. To illustrate this practice, the phase diagram of the Bisphenol-A and Phenol binary system is used as an example, as shown in FIGS. 2A and 2B.

The incongruent melting point (I) is the point where the adduct melts, and the liquid composition and the solid composition are not the same. When the adduct of phenol and bisphenol-A melts, the liquid composition is at point I while some solid bisphenol-A is formed as well. This is why the location of the adduct A is between point I and pure bisphenol-A.

There are two important regions or compartments in the phase diagram for production of bisphenol-A. One is the bisphenol-A compartment and the other is adduct compartment. When the feed composition to the crystallizer is located inside the bisphenol-A compartment, pure solid Bisphenol-A is recovered. When the feed composition to the crystallizer is located in the adduct compartment, solid adduct is recovered.

Figures 2A, 2B:
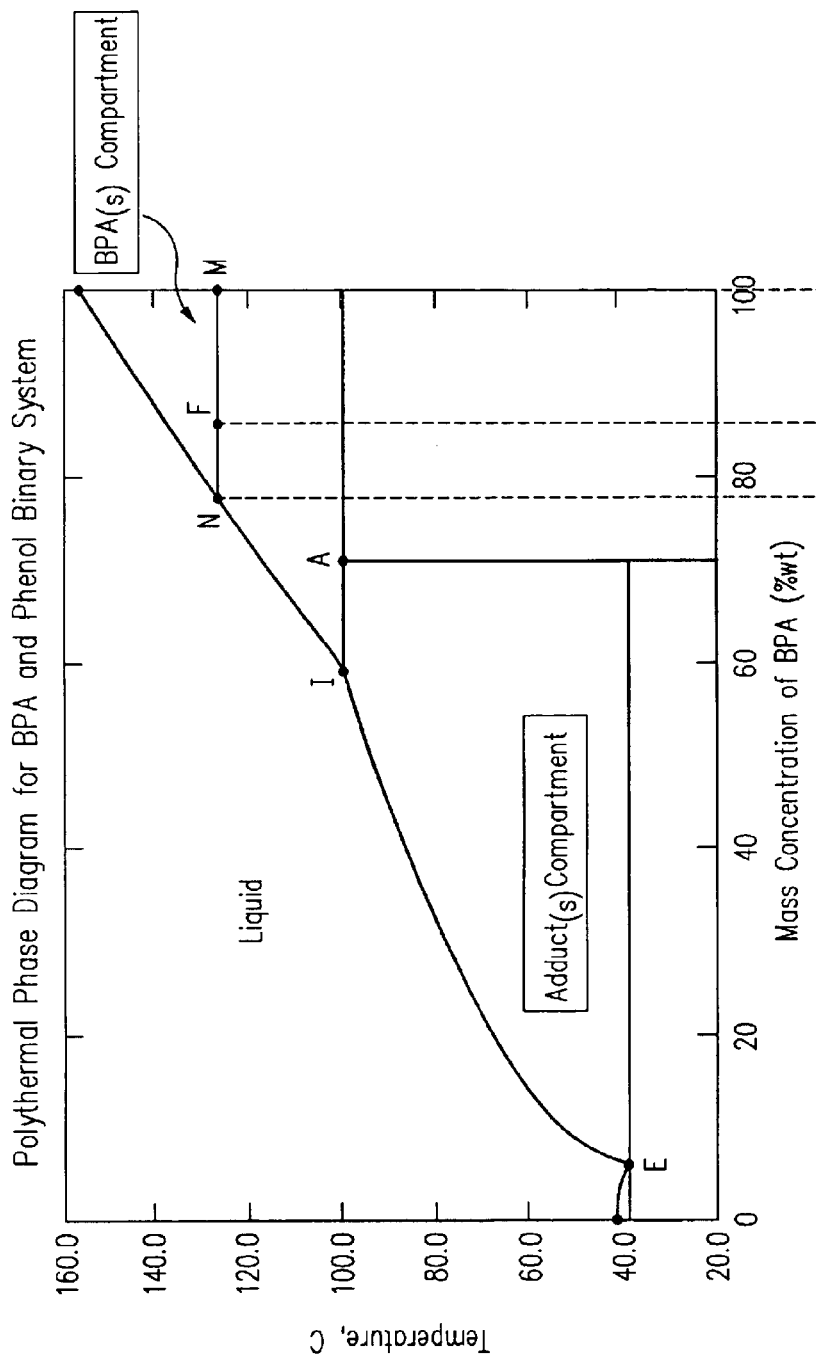
FIG. 2A is a polythermal phase equilibrium diagram for a binary system of bisphenol-A and phenol.
FIG. 2B is the projection of the polythermal diagram for the binary system of FIG. 2A.

To generate a projection of the polythermal phase diagram, the first step is to project the point of the intersection of two curves in FIG. 2A on the line in FIG. 2B. These points include pure phenol, eutectic point for phenol and adduct (E), the incongruent melting point (I), the adduct (A), and pure bisphenol-A, as shown on the line below the polythermal phase diagram FIG. 2A.

The temperature at each point can be marked on the projection of the polythermal diagram. For example, the temperature at point I is about 100° C. and the temperature at point M is about 135° C., as shown on FIG. 2A. However, the temperature is usually omitted during the initial process synthesis because the projection of the polythermal diagram is used to synthesize the process feasibility. The temperature effect can be considered later.

When the 2D phase diagram is reduced into 1-D projection of the polythermal diagram, the bisphenol-A compartment becomes one segment of the line IM. The adduct compartment becomes one segment of the line EA. When the feed composition in the product solution fed to the crystallizer is located in the bisphenol-A compartment, the recovery of bisphenol-A in the polythermal phase diagram can be easily projected on the polythermal phase diagram. The recovery of bisphenol-A can be defined as the ratio of the mass of pure bisphenol-A solid recovered to the mass of the feed. As illustrated in the Figures, the recovery of bisphenol-A is the ratio of FN to MN in this case. When the feed composition is kept the same and the temperature is reduced further, the recovery of bisphenol-A is increased. The maximum recovery of pure solid bisphenol-A is ratio of IF to IM because both bisphenol-A and adduct solid would co-exist if temperature is lowered to about 100° C.

The projection of the polythermal diagram can be employed as a useful tool for process feasibility study because it provides the region for product recovery. If the feed composition in the product solution fed to the crystallizer is located between point I and point M, solid bisphenol-A is recovered and the bisphenol-A recovery can be calculated easily. If the feed is located between E and I, solid adduct is recovered and the adduct recovery can be calculated.

The projection of the polythermal diagram becomes very useful when the complete phase diagram is 3-D or 4-D. The process alternatives can be easily visualized as described in this invention. FIGS. 3A to 7 illustrate projections of the polythermal phase diagrams according to the present invention and show how the various phase equilibrium regions are selectively controlled by adjusting the composition and/or concentration of the solvent in the product solution. The isobaric phase diagram of the ternary system of phenol, bisphenol-A and solvent represents an image in 3-dimensional space. The composition coordinates can be plotted in weight fractions on a triangular grid, and the temperature can be plotted on an additional vertical axis. However, it is not convenient to work with multi-dimensional phase diagrams. Fortunately, for this three component system, much of the important information, particularly the crystallization boundaries, can be represented on a 2-dimensional projection onto a triangular base. This is referred to as the projection of a polythermal phase equilibrium diagram. Please note that the ternary phase equilibrium diagrams are represented as right-angled triangular diagrams for clarity as opposed to the alternative equilateral triangular diagram form.

The present invention is now described in more detail. In contrast to the prior art, the inventors have discovered a system and method of producing bisphenol-A wherein three components are employed: bisphenol-A, phenol and solvent and the ternary phase conditions are selectively controlled. This is a very powerful tool and allows one to generate a phase equilibrium diagram with process operating conditions such as, but not limited to, type of solvent(s); concentration ratio of solvents when two or more solvent components are employed; mass concentration of any one of, or combination of, phenol, bisphenol-A and solvent fed to the crystallizer; feed rate of any one of, or combination of, the reactants fed to the condensation reactor; or recycled feed rates of any of the relevant constituents.

In general, in one embodiment of the present invention a method of producing bisphenol-A from a reaction forming a product solution is provided and where the product solution is comprised of phenol, bisphenol-A, isomers of bisphenol-A, and un-reacted reactants. A solvent is provided in the product solution. The solvent may be added to the product solution after the reaction. Alternatively, at least a portion of the solvent may already be present in the product solution following the reaction. The product solution is fed to a crystallizer and the phase equilibrium behavior of this feed stream to the crystallizer is selectively controlled by providing the product solution having a certain composition, such that either crystalline bisphenol-A or an adduct of bisphenol-A and phenol is crystallized from the product solution. The phase equilibrium behavior is selectively controlled most usually by controlling the concentration of the solvent in the product solution. However, the concentration of the other components in the product solution may also be controlled.

The solvent may be comprised of one component, or alternatively may be comprised of a mixture of two or more solvents components. Since acetone is a reactant and is present in the system, it is useful to employ as a solvent. However, may other components may be used as a solvent. Suitable solvents include but are not limited to: water; ketones such as acetone, MEK and MIBK; alcohols such as methanol, ethanol, NPA, IPA, 2-BuOH, t-BuOH, and 1,2-EG; ethers such as ethylene glycol monomethyl ether, 2-MeO Ethanol, 2-EtO Ethanol, 2-BuO Ethanol, and furfuryl alcohol; amides such as DMF, DMA, NMP and DMSO; and hydrocarbons such as aromatic hydrocarbons.

In another embodiment of the invention, the solvent is comprised of a mixture of two or more solvent components. In this embodiment, the solvent mixture is made of least a first solvent component which exhibits a first phase behavior, and at least a second solvent component which exhibits a second phase behavior. The impact on the phase behavior from the first and second solvent components is also related to the solubility of bisphenol-A in each of the first and second solvents. Thus, the solvent may be characterized in terms of its impact on the phase behavior of the system.

In another embodiment of the invention, the solvent is comprised of a mixture of two or more solvent components. In this embodiment, the solvent mixture is made of at least a first solvent component which produces a first phase behavior in the system, and at least a second solvent component which produces a second phase behavior in the system. The phase behavior of the system results from the mutual interaction of all the components present in the system; however, binary solubility data for bisphenol-A in various solvents and phenol in various solvents, may be used as a starting point to provide some indication of the type of phase behavior that may result for the complete system. The binary solubility data alone is not sufficient to determine the phase behavior of the complete system, however the binary solubility data is a useful guideline for initial selection of the solvent component. Thus, the solvent is characterized most preferably in terms of its impact on the phase behavior of the system. Additionally or alternatively, the solvent may be characterized less reliably in terms of the relative binary solubility of bisphenol-A and phenol in the solvent. When using solubility as the guideline for solvent selection, routine experimentation is performed within the teaching of the present invention to evaluate the suitability of the selected solvent.

In one preferred embodiment, when the solvent is comprised of a mixture of solvent components, the at least first and second solvent components exhibit at least first and second phase behaviors in the system that are diverse. Alternatively, the effect of the first and second solvent components on the phase behavior of the system may be closer, or similar, to each other.

When characterized in terms of binary solubility, in particular the binary solubility of bisphenol-A in the solvent component, the first and second solvent components exhibit solubilities that are preferably opposite; that is, one of the solvent components exhibits a higher solubility for bisphenol-A, relative to the other solvent component which exhibits a lower solubility for bisphenol-A. Alternatively, the solubilities of bisphenol-A in the first and second solvent components may be closer to each other.

However, to provide the greatest flexibility in the operation of the process, it is preferable to employ solvent components which provide the more diverse phase behavior in the system.

In the one embodiment where the first and second solvent components are selected to exhibit diverse phase behavior effect, the solvent components may be classified as "good" and "poor" solvents. The characterization of a good or poor solvent is determined with respect to bisphenol-A and may be described with reference to the phase diagrams shown particularly in FIGS. 3A, 3B and 4. As described further below, looking at the bisphenol-A compartment, a good solvent provides a smaller bisphenol-A compartment than a poor solvent which provides a larger bisphenol-A compartment. In other words, bisphenol-A has greater solubility in a good solvent than a poor solvent with respect to the solubility of the other component—i.e. phenol—in the same solvent. Thus, solubility is defined relative to one component of the phase equilibrium system, namely the bisphenol-A component. As a general principle, it is the effect a particular solvent has on the phase behavior, i.e. the size and location of the boundaries of the phase compartments that characterizes the solvent. For preliminary solvent selection, the binary solubility of solvent components may useful as a guideline for evaluating suitable candidates of solvents. As a guideline and for illustration purposes and without limiting the general teaching of the foregoing and in no way intended for limitation, examples of solvents which may be considered as good solvents include solvents which exhibit binary solubility values in the range of approximately 150 g bisphenol-A/100 g solvent to 25 g bisphenol-A/100 g solvent at room temperature. Examples of poor solvents include solvents which exhibit binary solubility values in the range of approximately 0.1 g bisphenol-A/100 g solvent to 50 g bisphenol-A/100 g solvent at room temperature.

Of significant advantage, the present invention provides for the selective control of the phase equilibrium behavior of the system. More specifically, when two or more solvent components are employed, the concentration ratio of the solvent components in the product solution is selected to control the phase equilibrium behavior to form either substantially pure solid bisphenol-A or an adduct of bisphenol-A and phenol from the product solution during crystallization. When only one solvent is employed, the concentration of that solvent in the product solution is selected to control the phase equilibrium behavior to form either substantially pure solid bisphenol-A or an adduct of bisphenol-A and phenol from the product solution during crystallization. When a mixture of solvent components is used, and the mixture is comprised of at least a good solvent and a poor solvent, the concentration ratio of good to poor solvents may be generally in the range of 1:100 to 100:1, and more usually in the range of about 80:20 to 20:80.

Figures 3A, 3B:
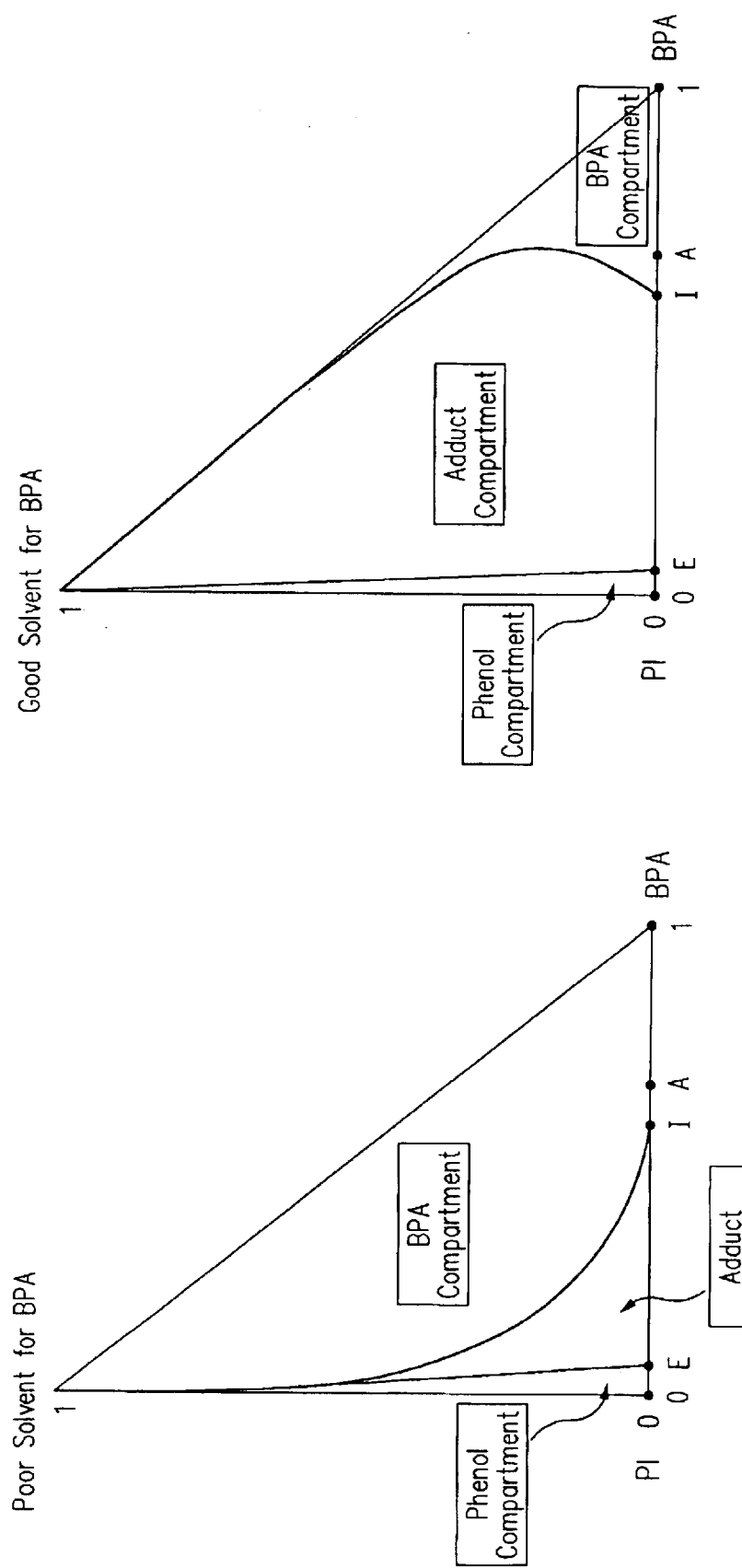
FIGS. 3A and 3B illustrate manipulation of a projection of the polythermal phase equilibrium diagram for a ternary system of bisphenol-A, phenol and solvent according to two embodiments of the present invention.
Figure 4:
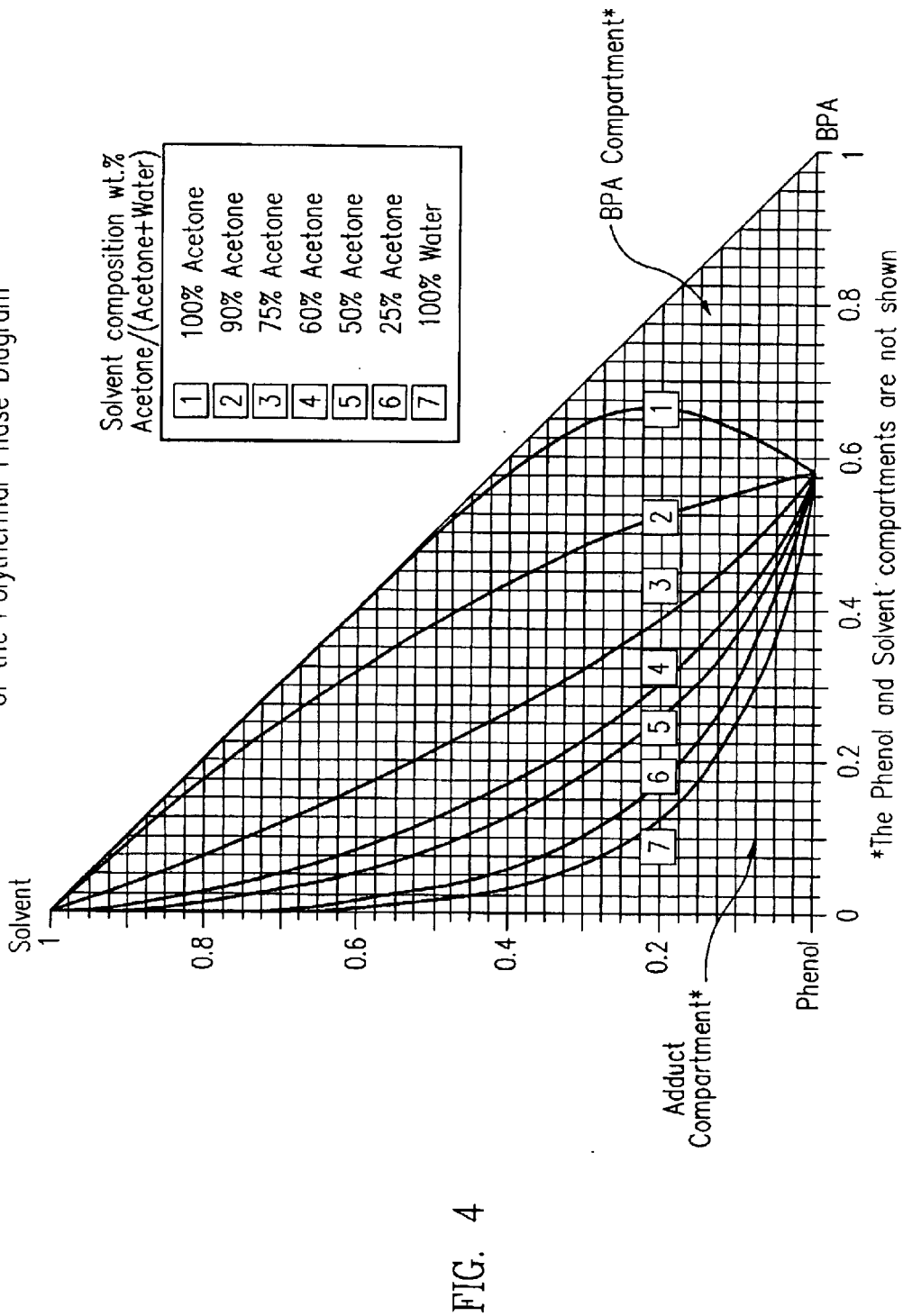
FIG. 4 is a projection of a polythermal phase equilibrium diagram for a ternary system of bisphenol-A, phenol and solvent showing manipulation of phase regions as a function of the composition of the solvent according to the present invention.

Referring to FIGS. 3A, 3B and 4 it is shown that bisphenol-A, phenol and the solvent are in phase equilibrium and exhibit phase behavior which establishes at least two regions or compartments in the phase diagram, an adduct phase compartment and a pure solid bisphenol-A phase compartment. A phenol phase compartment and a solvent compartment are also present, but are not discussed in detail since it they are not of significant interest to the teaching of the present invention. The phenol compartment typically occupies less than 2.5% of the entire area of the projected right angle phase diagram and does not affect the area of the bisphenol-A compartment. The location of the boundary of the compartment, and thus the size of the adduct compartment and the bisphenol-A compartment, are selectively controlled or manipulated by adjusting the composition of the solvent, or in the case where the solvent is a mixture, by adjusting the concentration ratio of the two or more solvent components. This is depicted with particular clarity in FIGS. 3A, 3B and 4 which show the change or "swing" in the size or shape of the adduct and bisphenol-A regions over a range of exemplary solvent compositions and concentrations. Those of ordinary skill in the art will recognize that the size of the compartments may move somewhat if impurities or other components are present in the product solution.

It is important to note that although the feed solution to the crystallizer is comprised of a multitude of components, including unreacted reactants and byproducts of the reaction, for process synthesis purposes it is sufficient to consider only the principal components. The principal components are phenol, bisphenol-A and the solvent (a pseudo-component generically referred to as the solvent). As discussed above, the solvent component may be a single component. More typically, the solvent is comprised of a mixture of components, such as a mixture of unreacted acetone, water formed in the reactor, and any other components which may act as solvents for bisphenol-A, and which may be introduced into the system either before the reaction step and/or before the crystallization step. The system of phenol, bisphenol-A and the solvent is treated as a ternary phase equilibrium system whose phase behavior will depend on the exact nature of the solvent.

Referring again to FIGS. 3A and 3B, manipulation of the phase equilibrium using two or more solvents with different phase behavior is shown according to two embodiments of the present invention. In general, size or shape of the adduct and bisphenol-A phase compartments are dependent upon the type of solvent present in the product solution. The terms size or shape of the compartment is meant to mean the size of the compartment in the projection of the polythermal phase diagram as shown in FIGS. 3A and 3B, and not the complete polythermal phase diagram. As illustrated, the two phase compartments are complementary, that is when the bisphenol-A compartment increases the adduct compartment decreases. FIG. 3A shows how the phase equilibrium behavior is controlled when using a solvent having poor solubility for bisphenol-A, such as but not limited to water. In this instance the solvent is comprised of 100% water which provides a large bisphenol-A region. In FIG. 3B, the bisphenol-A compartment is significantly decreased and the adduct compartment is significantly increased when a solvent having good solubility for bisphenol-A is used, such as but not limited to acetone. In this instance the solvent is comprised of 100% acetone. It should be noted that the phenol compartment is not to scale but is presented here for schematic illustration purposes.

Referring to FIG. 4, the definition of a good and poor solvent is further described. Here the polythermal projection of the phase diagram is plotted using grid paper and the total area or space of the projected phase diagram may be calculated. In this example, the total area of the right angle triangle is 0.5 (wt. fraction)$^2$. Then, the phase behavior effect of a good or poor solvent can be seen by the size of bisphenol-A compartment produced. In this example where the projected phase diagram is represented as a right angle triangle, a good solvent exhibits a bisphenol-A compartment having an area of approximately 0.4 (wt. fraction)$^2$ or less which corresponds to approximately 75% or less of the total projected phase diagram composition space. More typically, a good solvent exhibits a bisphenol-A compartment having an area in the range of approximately 5% to 70% of the total projected phase diagram composition space, and more preferably in the range of approximately 10% to 60% of the total projected phase diagram composition space.

A poor solvent is also characterized in this manner. Again, in this example, the total area is 0.5 (wt. fraction)$^2$. Where the projected phase diagram is represented as a right angle triangle, a poor solvent exhibits a bisphenol-A compartment having an area of approximately 0.26 (wt. fraction)$^2$ or greater which corresponds to approximately 50% or greater of the total projected phase diagram composition space. More typically, a poor solvent exhibits a bisphenol-A compartment having an area in the range of approximately 60% to 95% of the total projected phase diagram composition space, and more preferably in the range of approximately 70% to 90% of the total projected phase diagram composition space.

Given the teaching of the present invention, ternary phase equilibrium diagrams for different solvent compositions and/or concentration ratios may be created by those of ordinary skill in the art without undue experimentation. For example, computer simulation programs and thermodynamic databases may be used to develop the approximate location of the boundary of the bisphenol—and adduct compartments for different types of solvents and/or concentration ratios. The boundary between the adduct compartment and the bisphenol-A compartment is the trajectory of incongruent melting points. The incongruent melting point is the location where both bisphenol-A and adduct solid coexist. The maximum recovery of bisphenol-A is the maximum amount of bisphenol-A solid that can be recovered before adduct solid appears (or coexists with the bisphenol-A solid).

More specifically, the establishment of a thermodynamic model for the multi-component solid liquid equilibrium requires both theoretical calculation and experimental data for the model verification. Those of ordinary skill in the art can develop such thermodynamic models using known principles and tools.

The physical properties of the each component in the solution feed to the crystallizer such as the heat of fusion, melting point, and heat capacity are used to establish the thermodynamic model. The equilibrium relationship between the components and adduct as a function of temperature is needed. The binary interaction parameter among the components in the solution is either estimated or determined from experimental data. The theory for the activity coefficient is well developed, and a computer software program providing numerical methods for solving simultaneous non-linear equations is typically used. Examples of suitable commercially available software programs for thermodynamic model establishment include PropertiesPlus from Aspen Technology Inc., HYPROP III from Hyprotech, and ProPred from CAPEC at the Technical University of Denmark. The thermodynamic model is for the calculation of the concentration of the component when it is saturated and is a function of temperature and concentration. Since the effect of pressure on the saturation is not very significant in the pressure range considered, the pressure effect is not taken into account in this thermodynamic model; however, the analysis may be extended to consider the pressure effect if desired.

The region of the bisphenol-A compartment can be determined if the trajectory of the incongruent melting points can be determined. Since the incongruent melting point occurs when both adduct and bisphenol-A are saturated, this trajectory can be calculated from the thermodynamic model by those of ordinary skill in the art. The regions for the phenol compartment can be calculated once the trajectory of the eutectic point is determined. This trajectory can be also calculated by those of ordinary skill in the art from the thermodynamic model since the eutectic points occur when both phenol and adduct are saturated. The region between the phenol compartment and the bisphenol-A compartment in the concentration diagram is the adduct compartment. The temperature along the trajectory of incongruent melting points and the trajectory of the eutectic points is also be determined from the thermodynamic model by known techniques.

Figure 5:
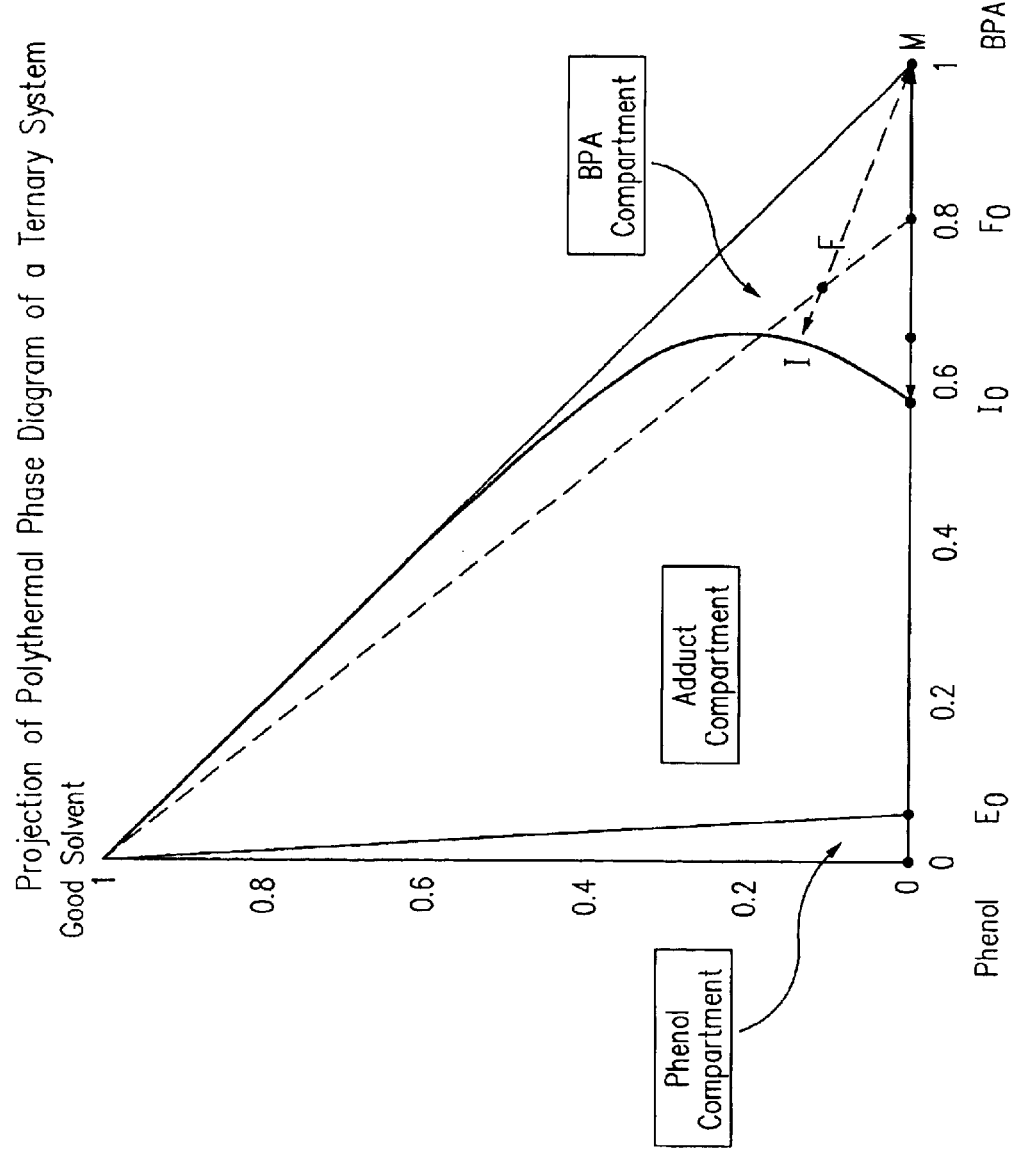
FIG. 5 is a projection of a polythermal phase equilibrium diagram for a ternary system of bisphenol-A, phenol and solvent showing maximum bisphenol-A recovery at a specific feed composition to a crystallizer according to one embodiment of the present invention.

As described above the present invention provides for selectively controlling the phase equilibrium regions or compartments of adduct and bisphenol-A during crystallization by adjusting the composition of the solvent present in the product solution to form a feed solution to a crystallizer having a certain feed composition such that either adduct or substantially pure bisphenol-A is produced. As such, the present invention provides a powerful tool allowing one to selectively operate the bisphenol-A system to generate the desired phase equilibrium region. This is illustrated in detail in FIGS. 5 to 9. Referring to FIG. 5, a projection of the polythermal ternary phase diagram is shown for components bisphenol-A, phenol and a solvent which in this instance may be characterized as a good solvent for bisphenol-A. In this exemplary embodiment, the solvent is a single solvent, and for example may be comprised of acetone. As described above, the presence of 100% acetone in the product solution establishes the location of the boundary and thus the size of the adduct and bisphenol-A compartments, respectively, as shown in FIG. 5. Once these phase equilibrium compartments are fixed, the present invention allows one to vary the composition of the product solution to produce a feed solution to the crystallizer (also referred to as the feed composition to the crystallizer) to fall within a desired one of the phase equilibrium compartments. For example, when it is desirable to form bisphenol-A in the crystallizer, the feed solution is provided having a feed composition of F which locates the feed composition at point F on the ternary diagram—i.e. in the bisphenol-A phase compartment. The feed composition F includes bisphenol-A, phenol and solvent. The maximum recovery of bisphenol-A crystals can be calculated by the well known lever (or mixture) rule, which is this example will be the ratio of the distance of line IF to IM. For theoretical comparison, a solvent free case is shown (i.e. no acetone in the feed composition) which produces a binary phase diagram. This is represented as $F_o$ on FIG. 5, and provides a maximum bisphenol-A recovery that is equal to the ratio of the distance of line $I_o F_o$ to $I_o M$.

Figure 6:
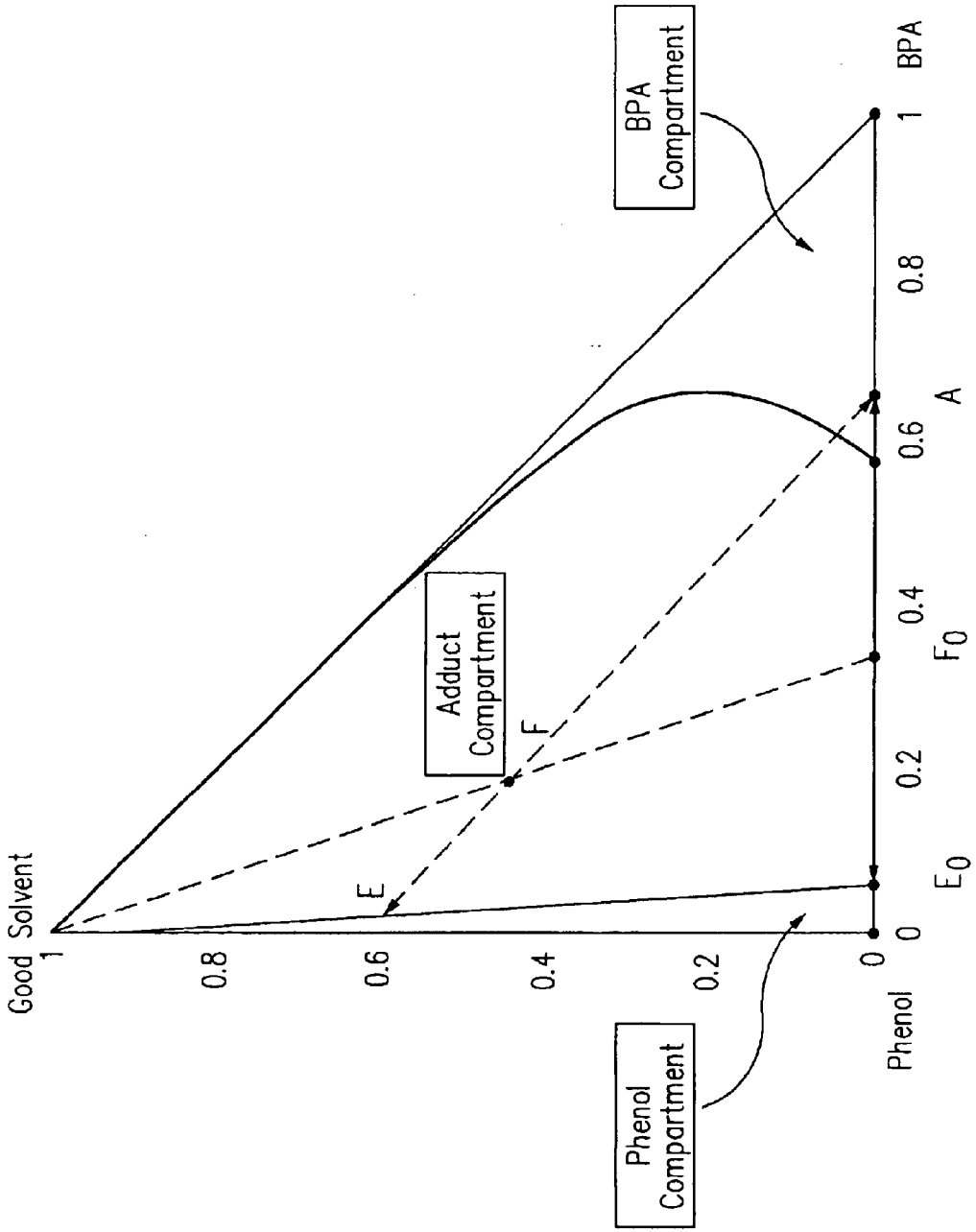
FIG. 6 is a projection of a polythermal phase equilibrium diagram for a ternary system of bisphenol-A, phenol and solvent showing maximum adduct recovery at a specific feed composition to a crystallizer according to one embodiment of the present invention.

FIG. 6 illustrates the case where it is desirable to form adduct in the crystallizer. In this example, the feed solution to the crystallizer has a feed composition of F which locates the feed composition at point F on the ternary diagram—i.e. in the adduct phase compartment. Again, applying the lever rule the maximum adduct recovery is the ratio of the distance of line EF to EA. For theoretical comparison, a solvent free case is shown (i.e. no solvent in the feed composition) which produces a binary phase diagram. This is represented as $F_o$ on FIG. 6, and provides a maximum adduct recovery that is equal to the ratio of the distance of line $E_o F_o$ to $E_o A$.

Figure 7:
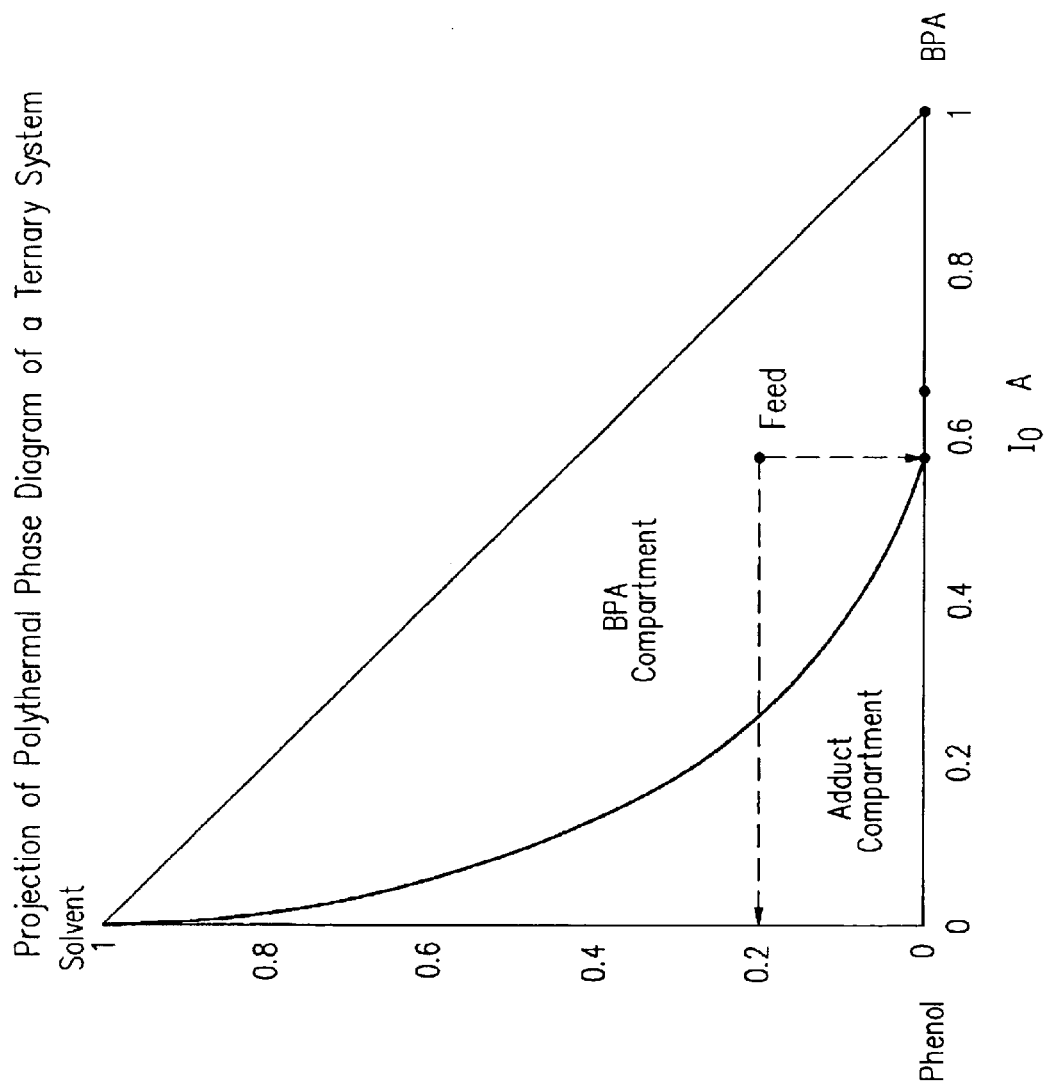
FIG. 7 is a projection of a polythermal phase equilibrium diagram for a ternary system of bisphenol-A, phenol and solvent according to one embodiment of the present invention.
Figure 8:
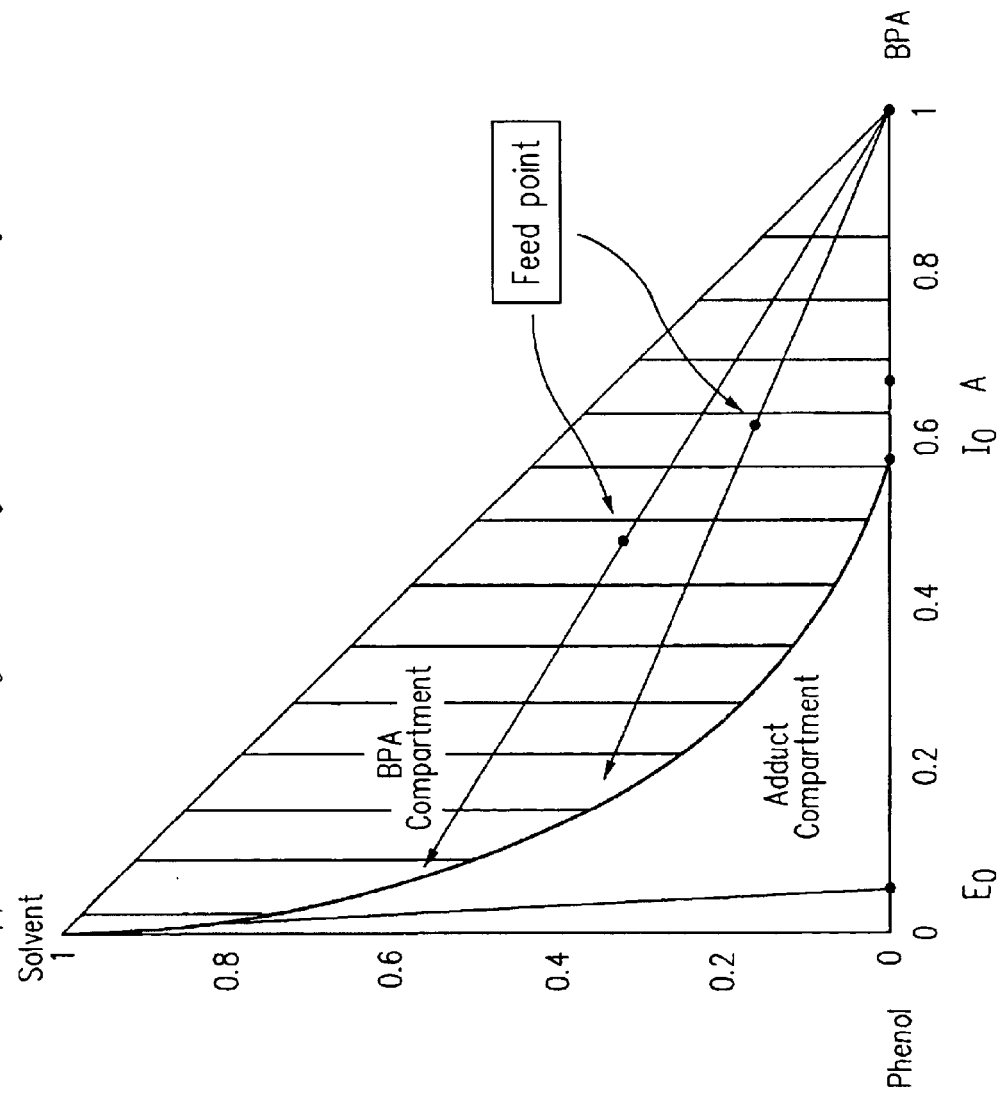
FIGS. 8 and 9 show projections of polythermal phase equilibrium diagram for a ternary system and illustrate the selective control of the size of the regions of the ternary phase diagram and adjustment of the feed composition to fall within a desired location on the ternary diagram in accordance with the method of the present invention.
Figure 9:
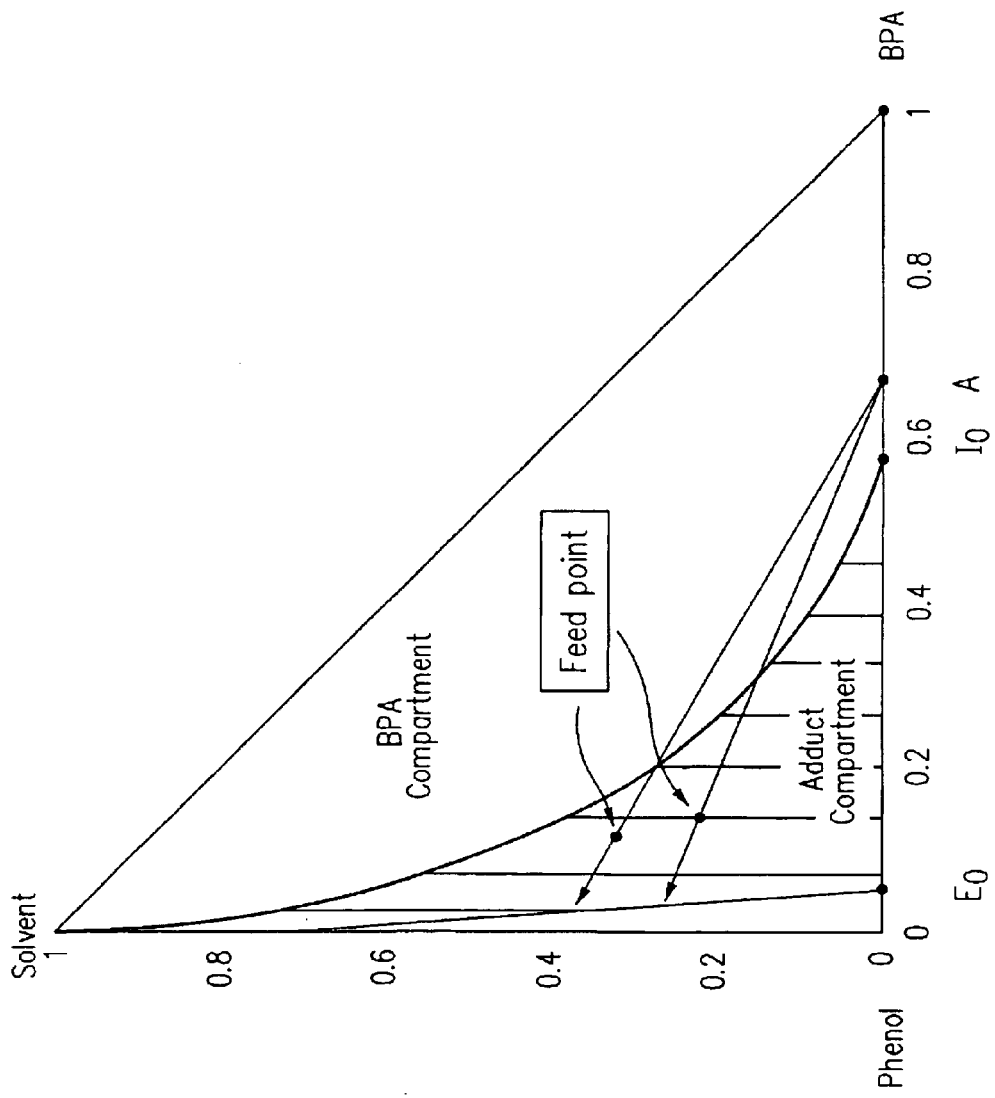

FIG. 7 shows a projection of the polythermal ternary phase equilibrium diagram and illustrates another embodiment of the present invention wherein the solvent is comprised of a two or more solvent components, in this example a mixture of acetone and water at a weight % concentration ratio of 50:50 acetone to water. Bisphenol-A has a higher solubility in acetone relative to water and results in a phase behavior that characterizes acetone as a good solvent and water as a poor solvent using the terminology herein. In this example it is desired to form bisphenol-A in the crystallizer. Accordingly, the feed composition is adjusted so that it falls within the bisphenol-A phase compartment on the phase diagram. In this example the feed solution has a feed composition of about 60 wt % bisphenol-A, 20 wt % acetone and water mixture, and 20 wt % phenol. Of course those of ordinary skill in the art will recognize that the feed composition to the crystallizer may vary as shown in FIGS. 8 and 9, and the only limitation is that the weight percent of the specific components in the feed composition fall within the selected compartment.

To selectively control the location of the composition in the product solution at the feed to the crystallizer, the composition of the various components in the product solution may be adjusted to certain amounts (typically weight or mol percent) to place the feed composition in the crystallizer at a location selectively within either the adduct or the pure solid bisphenol-A phase regions during crystallization. The composition of the product solution at the feed to the crystallizer may be adjusted in a variety of ways. Any one of, or combination of, phenol, bisphenol-A in solution, the solvent, or mixture of solvent components may be added to, or removed, from the product solution prior to the crystallizer to adjust the feed composition to the desired phase compartment. Alternatively, the composition of reactants fed to the reactor and the reaction conditions in terms of temperature, conversion, and the like may be adjusted to provide the desired composition in the product solution from the reactor. For example, the flow rate of phenol to the reactor may be varied to provide a certain weight or mol percent of phenol in the product solution. Examples of such flow rates are provided in illustrative embodiments shown in the Experimental section below. It should be understood that these examples are provided for illustration purposes only, and that many variations may be employed within the teaching of the present invention.

Figure 10A:
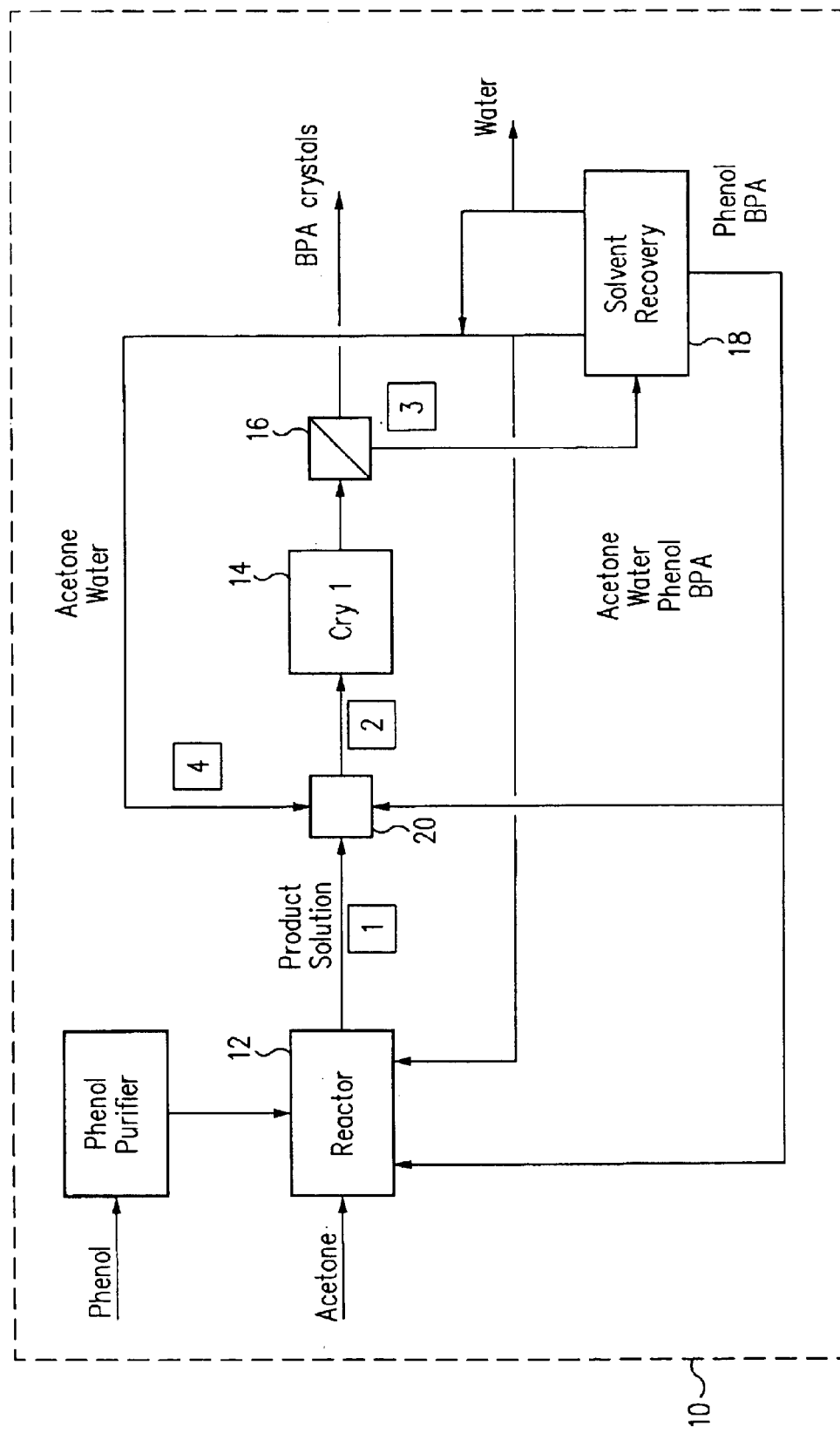
FIGS. 10A and 10B show a schematic process block diagram of a system for producing bisphenol-A, and corresponding projection of the ternary phase equilibrium diagram, respectively, according to one embodiment of the system and method of the present invention.
Figure 10B:
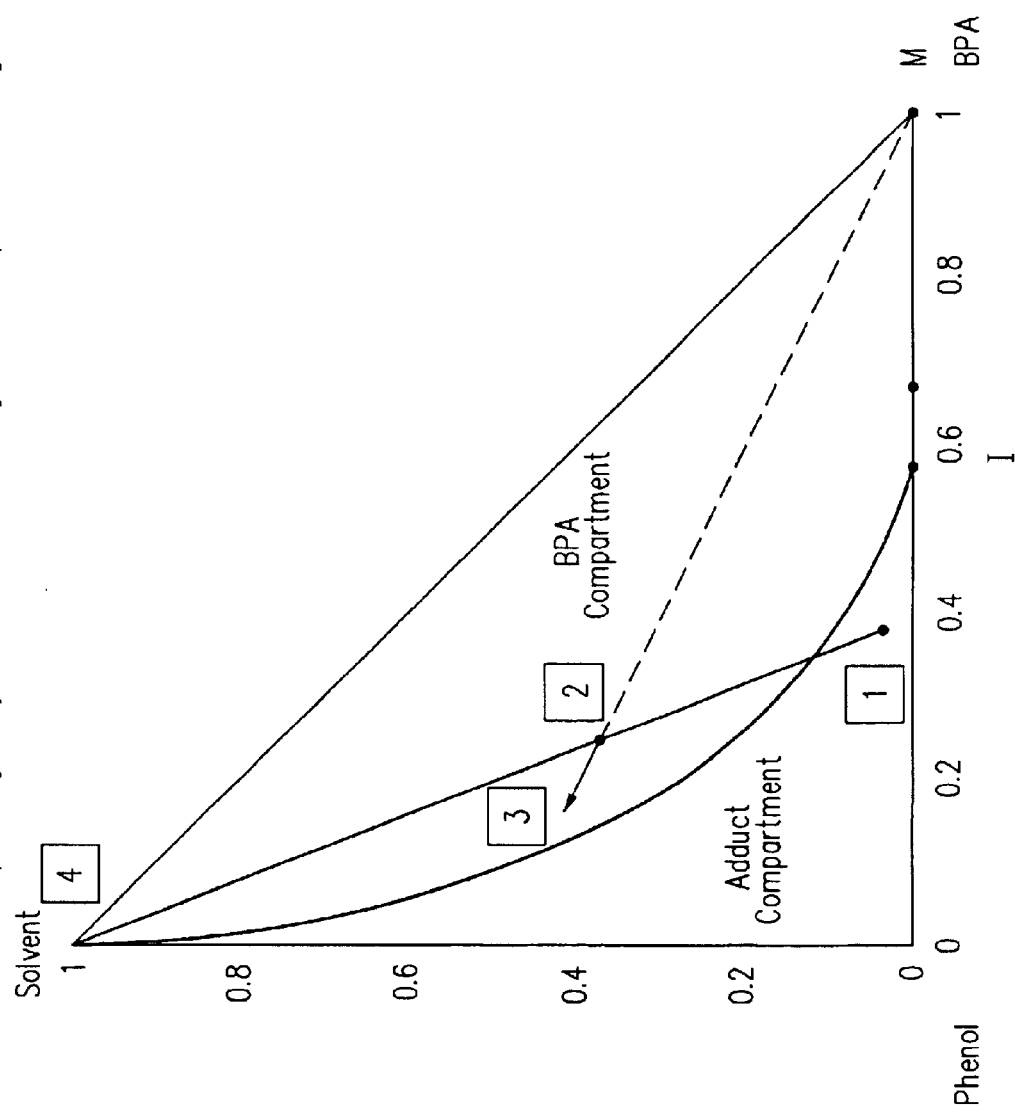
Figure 11A:
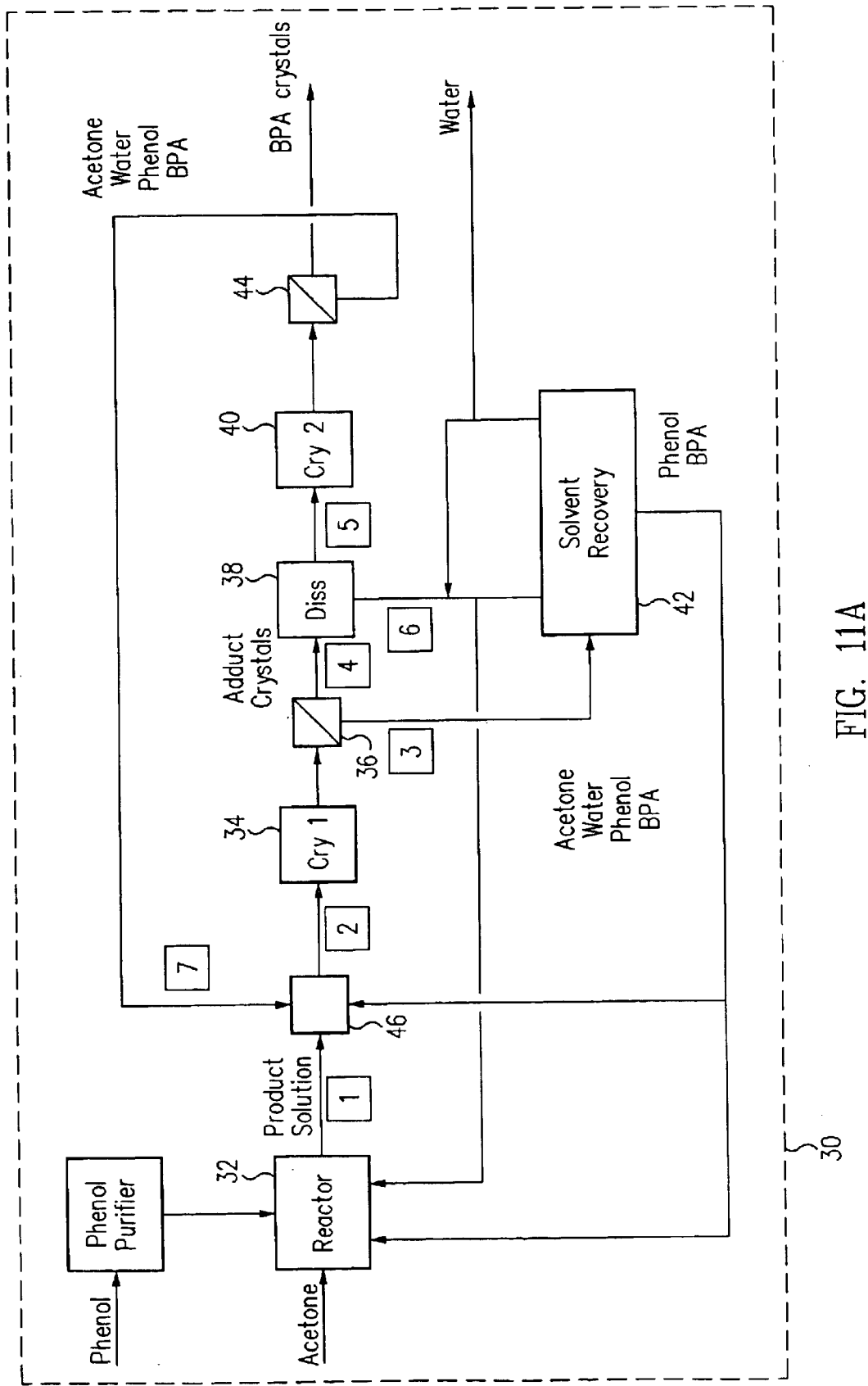
FIGS. 11A and 11B show a schematic process block diagram of a system for producing adduct and bisphenol-A, and corresponding projection of the ternary phase equilibrium diagram, respectively, according to an alternative embodiment of the system and method of the present invention.
Figure 11B:
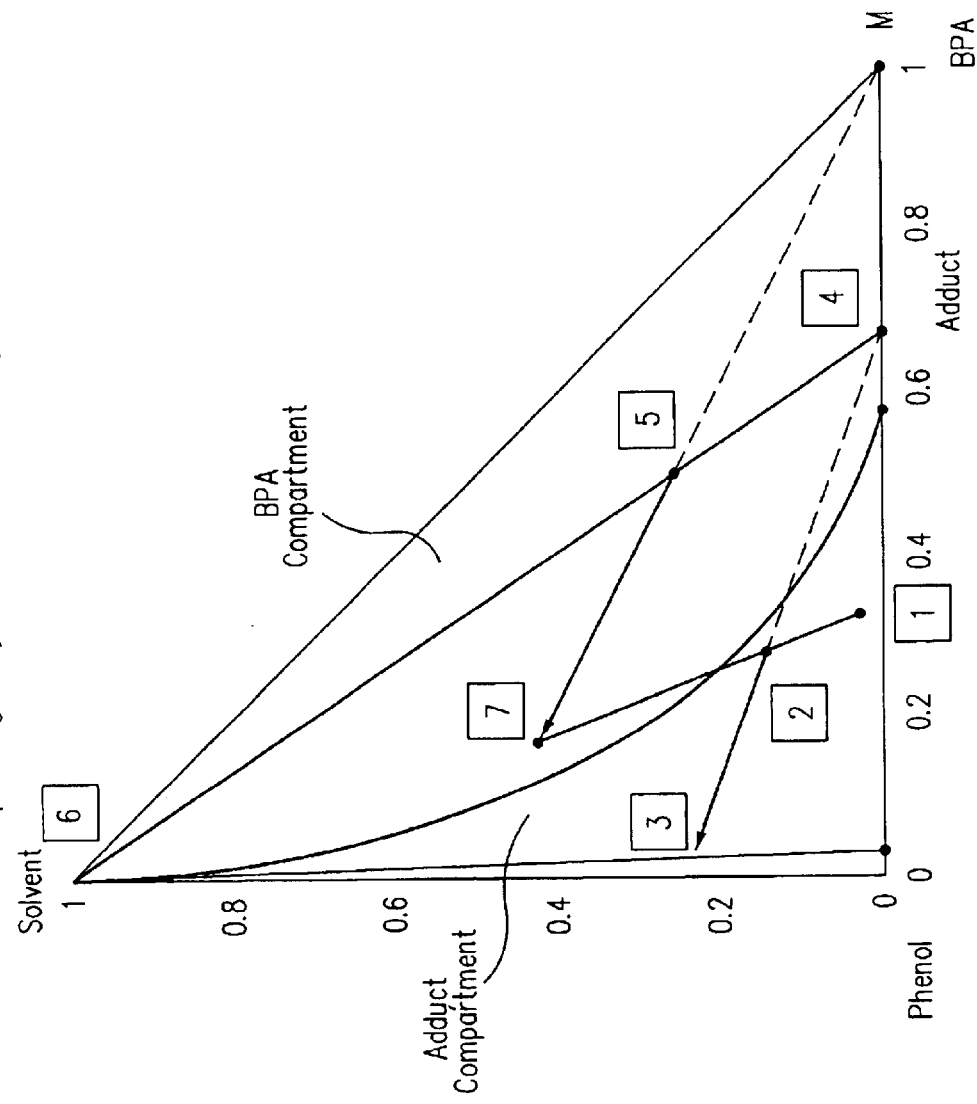

Of significant advantage, the present invention provides a powerful tool which allows one to tailor the design and operation of the bisphenol-A system depending upon the desired results. Referring to FIGS. 10A and 11A, schematic process block diagrams for bisphenol-A systems are shown according to two embodiments of the present invention. Corresponding projections of the polythermal ternary phase equilibrium diagrams are shown in FIGS. 10B and 11B, respectively.

In general as shown in FIG. 10A, one embodiment of the system 10 of the present invention is comprised of a fixed bed reactor 12, a single crystallizer 14, a solid-liquid separator (S/L) 16 and a solvent recovery unit 18. To form bisphenol-A, purified phenol preferably in stoichiometric excess, and acetone are conveyed to the fixed bed reactor 12 and passed through the fixed bed having an acid catalyst to produce a product solution in the liquid phase including bisphenol-A, unreacted reactants such as excess phenol, by-products of the reaction (such as water) and impurities such as isomers, analogs and homologs. The condensation reaction may be carried out at a temperature in the range of about 45° C. to 120° C., and more preferably about 50° C.

to 100° C. with about 75° C. being most preferred. The reaction pressure is in the range of about 1 to 8 bar, more preferably about 1 to 6 bar, with a reaction pressure of about 4.4 bar being most preferred.

To recover bisphenol-A the product solution is fed to the crystallizer 14. According to the present invention the composition of the product solution may be selectively adjusted in mixer/separator 20 prior to entering the crystallizer to produce a feed solution having a desired feed composition to the crystallizer 14 as described above.

In this embodiment the system of the present invention provides for one crystallizer. Advantageously, the system may be operated in such a manner to produce solid bisphenol-A directly from a one stage crystallizer 14, as opposed to forming the adduct of bisphenol-A and phenol. As described above a solvent, or mixture of solvent components are employed to establish the phase equilibrium regions for solid adduct and bisphenol-A as illustrated in FIG. 10B. The amount of each component in the product solution is adjusted to bring the composition of the feed solution to fall within the area of the bisphenol-A region or compartment. In one example shown in FIGS. 10A and 10B, the composition of the product solution is initially at point 1, which falls within the adduct region. To produce solid bisphenol-A during crystallization, solvent having a composition corresponding to point 4 in FIG. 10B is added to the product solution at mixer/separator 20 in an amount that brings the feed composition to point 2 which is within the bisphenol-A phase region as desired. The solvent may be added by any means, and preferably is added as one or more recycle streams from the solvent recovery unit 18. Known process control systems, such as on-line analysis with feedback control, may be used to selectively adjust the composition of the product solution at the feed to the crystallizer.

Having achieved the desired feed composition corresponding to point 2 on FIG. 10A, the product or feed solution is fed to the single crystallizer 14 whereupon cooling solid bisphenol-A is crystallized from the solution. Crystallizers are known in the art, and typically provide cooling by indirect or external cooling such as with heat exchanges or circulating cooling medium. Cooling may also be provided by pressure reduction, or by a combination of external heating and pressure reduction. In one example, the product solution is typically cooled to a temperature in the range of −30° C. to 160° C., more preferably to a temperature in the range of about 30° C. to 100° C. The crystallizer 14 is typically operated at a pressure in the range of about 0.1 bar to 6 bar, and the pressure range will be dependent on the type of solvent used and the crystallizer temperature, and the pressure should be selected such that the vapor fraction in the crystallizer is low or minimized. In an exemplary embodiment where acetone is employed as the solvent, the pressure in the crystallizer is in the range of about 0.5 bar to 6 bar, with about 3 bar being most preferred.

As cooling takes place, substantially pure bisphenol-A crystals form in the crystallizer 14. The residence time in the crystallizer in one example is in the range of about 1 to 10 hours, more typically in the range of about 2 to 5 hours. It should be understood that the optimum residence time is a function of the crystal growth rate in a given solvent, and thus the optimum residence times will vary depending on the type of solvent employed. Solid bisphenol-A is separated from the remaining solution (referred to as mother liquor or M/L) in the S/L separator 16. The mother liquor has a composition corresponding to point 3 in FIG. 10B. Any suitable type of S/L separator 16 may be used such as centrifuge or filtration and the like. The mother liquor contains phenol and solvent which are separated in the solvent recovery unit 18 and may be recycled to the reactor and/or added to the product solution to selectively adjust the feed composition prior to crystallization. The solvent recovery unit 18 may employ any suitable separation means such as distillation and the like. The bisphenol-A crystals are generally washed to remove any residual mother liquor Preferably the bisphenol-A crystals are washed with the solvent. Further purification steps may be employed if desired.

Those of ordinary skill in the art will recognize the significant advantages provided by the present invention. For example, since bisphenol-A crystals are formed in the crystallizer, the complex and costly dephenolation steps for removal of phenol from the adduct required by the prior art processes are absent.

An alternative embodiment of the system and method of the present invention is shown in FIGS. 11A and 11B. In this embodiment, the system selectively produces an adduct of bisphenol-A and phenol in a first crystallizer and then substantially pure solid bisphenol-A is formed in a second crystallizer. In general as shown in FIG. 11A, the system 30 of the present invention is comprised of a fixed bed reactor 32, a first crystallizer 34, a first S/L separator 36, a dissolution tank 38, second crystallizer 40, solvent recovery unit 42 and second S/L separator 44. Similarly as described above, purified phenol preferably in stoichiometric excess, and acetone are conveyed to the fixed bed reactor 32 and passed through the fixed bed having an acid catalyst to produce a product solution in the liquid phase including bisphenol-A, unreacted reactants such as excess phenol, by-products of the reaction (such as water) and impurities such as isomers, analogs and homologs. The condensation reaction is carried out at temperatures and pressures as described above in FIG. 10A.

In this embodiment the system of the present invention provides for two crystallizers, the adduct crystallizer 34 to form an adduct of bisphenol-A and phenol, and the second, or bisphenol-A, crystallizer 40 to form bisphenol-A crystals. Specifically, as described above a solvent, or mixture of solvent components are employed to establish the phase equilibrium compartments for solid adduct and bisphenol-A as illustrated in FIG. 11B. In the exemplary embodiment shown in FIGS. 11A and 11B, the solvent is a mixture of acetone and water. The product solution has an initial composition following the reaction as point 1, shown in both FIGS. 11A and 11B. The feed composition of the product solution fed to each of the adduct and bisphenol-A crystallizers 34 and 40 is adjusted such that the feed composition falls within the adduct phase compartment in the adduct crystallizer 34 and within the bisphenol-A compartment in the bisphenol-A crystallizer 40. The feed composition of the product solution at the adduct crystallizer 34 and the bisphenol-A crystallizer 40 is shown in FIG. 11A as point 2 and point 5, respectively. The corresponding location of the feed composition of the product solution on the projection of the polythermal phase diagram is also shown in FIG. 11b as point 2 and point 5 respectively.

More specifically, following the reaction, the product solution is fed to the first, or adduct, crystallizer 34. According to the present invention the composition of the product solution is adjusted in mixer 46 prior to entering the adduct crystallizer 34 to establish a feed solution having a feed composition at a location within the adduct phase region such that the adduct is formed upon crystallization. In this exemplary embodiment the feed composition of the product solution is adjusted from a composition corresponding to point 1 on FIG. 11B to a composition corresponding to point 2 by the addition of various components—in this case a recycle stream from S/L separator 44 comprised of solvent, phenol and bisphenol-A having a composition corresponding to point 7. While one example is shown here, solvent and/or other components may be added prior to each of the crystallizers 34 and 40 by any means; and preferably is recycled from the solvent recovery unit 42 and/or recycled from any one or both of the S/L separators 36 and 44. Also in some cases, solvent in the desired concentration may already be present in the product solution following the reaction and/or the first crystallizer 34, and thus physical addition of the solvent may not always be necessary.

Having achieved the desired feed composition for adduct crystallization, the product solution is fed to the adduct crystallizer 34 whereupon the first cooling step is conducted to crystallize solid adduct of phenol and bisphenol-A. The product solution is typically cooled in the adduct crystallizer 34 to a temperature in the range of —110° C. to 160° C., more preferably to a temperature in the range of about 30° C. to 80° C. The adduct crystallizer is typically operated at a pressure in the range of about 0.1 bar to 6 bar. In an exemplary embodiment, where acetone is employed as the solvent the pressure in the adduct crystallizer 34 is in the range of about 0.5 bar to 5 bar, with about 3 bar being most preferred to maximize the liquid fraction in the adduct crystallizer 34.

As cooling takes place, solid adduct of phenol and bisphenol-A form in the crystallizer 34. The residence time in the crystallizer is in the range of about 1 to 10 hours ideally, more preferably in the range of about 2 to 5 hours. The adduct is separated from the mother liquor in the first S/L separator 36. Any suitable type of S/L separator 36 may be used such as centrifuge or filtration. The mother liquor, having a composition corresponding to point 3 in FIG. 11B, is conveyed to the solvent recovery unit 42 where solvent and phenol are separated and recycled to the reactor, and/or added independently to mixer/separator 46 and dissolution tank 38 to adjust the feed composition as desired prior to crystallization. Upon separation the adduct will have a composition corresponding to point 4 in FIG. 11B. The adduct can be washed with purified phenol in S/L separator 36.

Following separation, the adduct is dissolved in dissolution tank 38 at an elevated temperature. The elevated temperature is selected to be above the melting temperature of the adduct, and is dependent upon the concentration of the solvent. In the preferred embodiment, the solvent is added to the dissolution tank to assist with dissolving the adduct. The solvent composition is established to selectively define the phase equilibrium bisphenol-A and adduct compartments as desired, and the composition of the product solution is adjusted to place the feed composition at the bisphenol-A crystallizer 40 within the desired bisphenol-A phase compartment. In this example, the composition of the product solution is adjusted by the addition of a recycle stream from the solvent recovery unit 42 which has a composition corresponding to point 6 on FIG. 11B. Preferably, solvent is added in the dissolution tank; however, the solvent may be added at any other location prior to the bisphenol-A crystallizer 40.

The dissolved adduct, having a composition corresponding to point 5 on FIG. 11B, is sent to the bisphenol-A crystallizer 40 to crystalize substantially pure bisphenol-A. The product solution is typically cooled in the bisphenol-A crystallizer 40 to a temperature in the range of about –30° C. to 160° C., more preferably to a temperature in the range of about 50° C. to 100° C. The crystallizer is typically operated at a pressure in the range of about 0.1 bar to 6 bar. Again, any suitable crystallizer may be used, and of particular advantage, the size of the bisphenol-A crystallizer 40 is smaller than the adduct crystallizer 34, and is smaller than crystallizers used in the prior art, since the feed to the crystallizer 40 is a mixture of adduct and solvent. In one exemplary embodiment the solvent composition is comprised of 25 wt. % acetone and 75 wt. % water as the adduct exhibits high solubility in this solvent mixture.

As cooling takes place, solid bisphenol-A crystals form. The residence time in the bisphenol-A crystallizer 40 is typically in the range of about 1 to 10 hours, more preferably in the range of about 2 to 5 hours. The bisphenol-A crystals are separated from the mother liquor in the second S/L separator 44, and the mother liquor is used to adjust the feed compositions in the crystallizer 34. The bisphenol-A crystals are preferably washed and dried to remove any residual solvent (not shown). The dry bisphenol-A crystals are now ready for further processing. Again, the costly and complex dephenolation steps for removal of phenol form an adduct required by the prior art are absent in the inventive system and method.

EXPERIMENTAL

Simulated experiments are provided below to further illustrate the system and method of the present invention. These simulated experiments are provided for illustration purposes only and are not intended to limit the scope of the invention in any way.

Example 1

For the simulated experiments, the following design basis was used: 70,000 MTA bisphenol-A (9,112 kg/hr); Acetone conversion in the condensation reaction of phenol with acetone is about 80%; Phenol to acetone feed molar ratio to the condensation reactor is 15; bisphenol-A recovery from adduct crystallizer is about 95%; and bisphenol-A recovery from the bisphenol-A crystallizer is about 85%.

In one example, the system units are as follows: The condensation reactor is a fixed type reactor having a size of about 200 $M^3$ at a flow rate of about 77 $M^3$/hr. The condensation reaction is carried out at a temperature of about 75° C., and at a reaction pressure of about 4.4 bar.

In this example, the adduct crystallizer is a circulating Magma Crystallizer with draft-tube-baffle (DTB), having a size of about 150 $M^3$ and receives a flow rate of about 84 $M^3$/hr. The crystallizer is at a temperature of about 51° C. to achieve of bisphenol-A recovery of about 95%. The temperature can be lowered slightly to increase the bisphenol-A recovery, and operates at a pressure of about 5 bar. The cooling duty is 1.2 mmKcal/hr for latent heat, and 0.4 mmKcal/hr for heat of fusion.

In this example, the solid/liquid separator (S/L) is a rotary pressure drum filter having a liquid flow rate of about 76,325 kg/hr (excluding the wash liquor) and has a solid flow rate of about 15,161 kg/hr. The S/L is operated at a temperature of about 51° C. and at a pressure of about 5 bar. Preferably the unit is gas tight due to the presence of acetone in the feed.

A dissolution tank is provided as a mixing tank with a heater. In the exemplary embodiment the tank has a size of about 0.53 $M^3$ and provides a residence time of about 0.3 hours. Of particular advantage the tank is smaller that prior art systems due to the use of acetone. The adduct exhibits good solubility in the acetone. Preferably the tank is operated at a temperature of about 90° C. and a pressure of about 5 bar. In this example the liquid flow rate is about 3,499 kg/hr and the solid flow rate is about 15,161 kg/hr.

The bisphenol-A crystallizer is a circulating Magma Crystallizer with DTB in this example, at a size of about 55 $M^3$ and is operated at a temperature of about 75° C. and a pressure of about 5 bar. The bisphenol-A crystallizer receives the feed at a flow rate of about 18.2 $M^3$/hr in this example. The cooling duty of the bisphenol-A crystallizer is about 0.3 mmKcal/hr for the heat of fusion. Of particular advantage the bisphenol-A crystallizer is only about 35% of the size of the adduct crystallizer due to the high solution of adduct in the mixture of acetone and water.

To separate the bisphenol-A crystals from the mother liquor following the bisphenol-A crystallizer, a centrifuge may be employed. Preferably a screen bowl centrifuge is used. In this example the centrifuge receives a liquid flow rate of about 9,534 kg/hr and a solid flow rate of about 9,126 kg/hr. The centrifuge is typically operated at a temperature of about 75° C. and a pressure of about 5 bar.

In the event washing is needed, the amount of washing is dependent upon the quality of the bisphenol-A product in terms of impurities on the bisphenol-A crystal surface. If re-crystallization is needed to improve the purity of the bisphenol-A crystals, it is preferred to use either acetone or a mixture of acetone and water as the solvent because the solubility of bisphenol-A in acetone is high and hence the size of the crystallizer and dissolution tank can be reduced.

Example 2

Simulated examples showing typical stream compositions for the major solution streams are provided, corresponding to the present invention as shown in FIG. 10A, using one crystallizer (Cryst. 1). Solution stream compositions are shown in Table 1 below and are in wt %, on an impurity free basis. Note, that impurities are typically present at the inlet and outlet of the reactor, however they are considered to be minimal. Examples of typical impurities, include but are not limited to: by-products such as 2,4-bisphenol-A, trisphenol, chromans, IPP dimers, and other higher condensation products. In this example, the solvent is comprised of a mixture of two solvent components; namely, acetone which is a good solvent for bisphenol-A, and water which is a poor solvent for bisphenol-A. The overall phenol to acetone ratio in the fresh feed is 2 on a mole basis.

TABLE 1

| Component | Reactor Feed Wt. % | Reactor Outlet Wt. % | Feed to Cryst. 1 Wt. % | M/L from Cryst. 1 Wt. % |
|---|---|---|---|---|
| Phenol | 70.69 | 59.60 | 53.16 | 60.41 |
| BPA | 24.97 | 38.42 | 34.27 | 25.32 |
| Acetone | 4.28 | 0.86 | 8.98 | 10.21 |
| Water | 0.06 | 1.12 | 3.58 | 4.07 |
| Total | 100.00 | 100.00 | 100.00 | 100.00 |

As shown, the composition of the product solution at the feed to Cryst. 1 is selectively provided such that pure bisphenol-A crystals are formed in Cryst. 1.

Example 3

Simulated examples showing typical stream compositions for the major solution streams are provided, corresponding to the present invention as shown in FIG. 11A, using two crystallizers, the adduct crystallizer (Cryst. 1) and the bisphenol-A crystallizer (Cryst. 2). Solution stream compositions are shown in Table 2 below and are in wt %, on an impurity free basis (same as noted in Example 2 above). In this example, the solvent is again comprised of a mixture of acetone and water, and illustrates a moderate "swing" in the solvent composition between the two crystallizers. The solvent compositions in both the crystallizers may be characterized to be in or near the poor solvent regime. The overall phenol to acetone ratio in the fresh feed is 2 on a mole basis. A high acetone conversion and high bisphenol-A recovery is obtained.

TABLE 2

| Component | Reactor Feed Wt. % | Reactor Outlet Wt. % | Feed to Cryst. 1 Wt. % | M/L from Cryst. 1 Wt. % | Feed to Cryst. 2 Wt. % | M/L from Cryst. 2 Wt. % |
|---|---|---|---|---|---|---|
| Phenol | 93.36 | 79.89 | 81.58 | 93.90 | 35.69 | 66.89 |
| BPA | 1.51 | 18.04 | 14.19 | 0.88 | 51.51 | 9.08 |
| Acetone | 5.08 | 0.58 | 0.42 | 0.01 | 0.01 | 0.02 |
| Water | 0.05 | 1.49 | 3.81 | 12.79 | 12.79 | 24.01 |
| Total | 100.00 | 100.00 | 100.00 | 100.00 | 100.00 | 100.00 |

As shown, the composition of each feed stream are selectively provided such that adduct is formed in Cryst. 1, and pure bisphenol-A crystals are formed in Cryst. 2.

Example 4

An additional simulated example showing typical stream compositions for the major solution streams are provided, corresponding to the present invention as shown in FIG. 11A, using two crystallizers, the adduct crystallizer (Cryst. 1) and the bisphenol-A crystallizer (Cryst. 2). The solution stream compositions are shown in Table 3 below and are in wt %, on an impurity free basis (same as noted in Example 2 above). In this example, the solvent is again comprised of a mixture of acetone and water, and illustrates a moderate-large "swing" in the solvent composition between the two crystallizers. The solvent utilized in the first crystallizer indicates a good solvent, and the solvent used in the second crystallizer indicates a poor solvent. The overall phenol to acetone ratio in the fresh feed is 2 on a mole basis. A high bisphenol-A recovery is obtained; however, the acetone conversion is lower, leading to a larger acetone recycle stream.

TABLE 3

| Component | Reactor Feed Wt. % | Reactor Outlet Wt. % | Feed to Cryst. 1 Wt. % | M/L from Cryst. 1 Wt. % | Feed to Cryst. 2 Wt. % | M/L from Cryst. 2 Wt. % |
|---|---|---|---|---|---|---|
| Phenol | 89.89 | 75.04 | 77.26 | 89.86 | 35.04 | 64.29 |
| BPA | 1.65 | 19.86 | 15.47 | 0.98 | 50.58 | 9.29 |
| Acetone | 8.27 | 3.30 | 2.57 | 3.24 | 0.99 | 1.83 |
| Water | 0.19 | 1.80 | 4.70 | 5.93 | 13.39 | 24.59 |
| Total | 100.00 | 100.00 | 100.00 | 100.00 | 100.00 | 100.00 |

Example 5

A further simulated example was conducted showing typical stream compositions for the major solution streams, corresponding to the present invention as shown in FIG. 11A, using two crystallizers, the adduct crystallizer (Cryst. 1) and the bisphenol-A crystallizer (Cryst. 2). The solution stream compositions are shown in Table 4 below and are in wt %, on an impurity free basis (same as noted in Example 2 above). In this example, the solvent is again comprised of a mixture of acetone and water, and illustrates a negligible "swing" in the solvent composition between the two crystallizers. The solvent utilized in both the first and second crystallizers are characterized as good solvents. The overall phenol to acetone ratio in the fresh feed is 2 on a mole basis. A high acetone conversion is obtained; however, the per pass recovery of bisphenol-A is low, which leads to a larger recycle stream around the crystallizers.

TABLE 4

| Component | Reactor Feed Wt. % | Reactor Outlet Wt. % | Feed to Cryst. 1 Wt. % | M/L from Cryst. 1 Wt. % | Feed to Cryst. 2 Wt. % | M/L from Cryst. 2 Wt. % |
|---|---|---|---|---|---|---|
| Phenol | 93.23 | 79.87 | 77.25 | 92.85 | 37.76 | 56.09 |
| BPA | 1.82 | 18.22 | 18.26 | 1.21 | 54.50 | 32.41 |
| Acetone | 4.92 | 0.46 | 1.81 | 2.39 | 3.59 | 5.34 |
| Water | 0.03 | 1.45 | 2.68 | 3.55 | 4.15 | 6.16 |
| Total | 100.00 | 100.00 | 100.00 | 100.00 | 100.00 | 100.00 |

Comparison of key variables for Examples 3 to 5 above can be summarized, and are shown below in Table 5, where "AT" stands for acetone, and "W" represents water.

TABLE 5

| Example number | Per Pass Acetone conversion (mol %) | Per Pass BPA recover (wt. %) | Solvent composition wt. % AT/(AT + W) | | Recycle flows as a % of flows in Example 3 Around | | |
|---|---|---|---|---|---|---|---|
| | | | Cryst. 1 | Cryst. 2 | Crysts.[a] | Phenol[b] | Acetone[c] |
| Example 3 | 90 | 91 | 9.8 | 0.1 | 100 | 100 | 100 |
| Example 4 | 61 | 90 | 35.4 | 6.9 | 107 | 88 | 492 |
| Example 5 | 91 | 60 | 40.3 | 46.4 | 208 | 106 | 45 |

[a]Stream 7 in FIG. 11A
[b]Phenol recycle from solvent recovery unit 42 in FIG. 11A
[c]Acetone recycle to reactor 32 from solvent recovery unit 42 in FIG. 11A In summary, it is shown that the present invention provides a powerful tool wherein numerous routes, system design and operating conditions can be manipulated from selective control of the phase equilibrium diagram. Process variables that can be manipulated to achieve a desired target include: solvent composition; adding, subtracting or reaction control coupled with process operations (crystallization) to bring the feed composition at the crystallizer to the desired region on the phase diagram; sequence can be altered to achieve the same target; and recovery can be controlled by temperature after the feed location in the phase diagram region is fixed.

The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

We claim:

1. A method for producing bisphenol-A by crystallization from a product solution comprising the following steps:
    forming a product solution comprised of phenol, bisphenol-A, isomers of bisphenol-A, un-reacted reactants, and a solvent comprised of two or more solvent components,
    selectively controlling the amount of said solvent in the product solution to manipulate a phase behavior of the product solution such that a maximum amount of substantially pure crystalline bisphenol-A will be crystallized from said product solution before a solid adduct of bisphenol A and phenol appears, where the total weight percent of said solvents prior to crystallization is at or below about 40%, and
    separating substantially pure bisphenol-A, where the final separation of substantially pure bisphenol-A is achieved by direct crystallization.

2. The method of claim 1 wherein said solvent is selected from any combination of water, ketones, alcohols, ethers, amides and hydrocarbons.

3. The method of claim 1 wherein said solvent is present in the product solution following the reaction that forms the product solution.

4. The method of claim 1 wherein the bisphenol-A, phenol and solvent exhibit a phase equilibrium relationship represented by a projection of a polythermal ternary phase diagram and where one of said solvent components produces a first phase behavior and the other of said solvent components produces a second phase behavior.

5. A method for producing bisphenol-A by crystallization from a product solution comprising the following steps:
    forming a product solution from a reaction comprised of phenol, bisphenol-A, isomers of bisphenol-A, un-reacted reactants, and a solvent comprised of two or more solvent components, where the bisphenol-A, phenol and solvent exhibit a phase equilibrium relationship represented by a projection of a polythermal ternary phase diagram having a total defined area and at least two regions in the phase diagram, an adduct region and a pure solid bisphenol-A region, where one of said solvent components exhibits a first phase behavior and the other of said solvent components exhibits a second phase behavior, and
    selectively controlling the concentration ratio of said solvent components in the product solution during crystallization, to produce a phase behavior such that substantially pure solid bisphenol-A will be crystallized from said product solution, where the total weight percent of said solvents prior to crystallization is less than about 40%, separating substantially pure bisphenol-A, where the final separation of substantially pure bisphenol-A is achieved by direct crystallization.

6. The method of claim 5 where the two or more solvent components are comprised of any one or more of the reactants and/or products formed from the reaction.

7. The method of claim 5 where said first phase behavior of one of said solvent components produces said bisphenol-A region having an area of approximately 75% or less of the total projected phase diagram area.

8. The method of claim 5 where said second phase behavior of one of said solvent components produces said bisphenol-A region having an area of approximately 50% or greater of the total projected phase diagram area.

9. The method of claim 5 where said first phase behavior of one of said solvent components produces said bisphenol-A region having an area in the range of approximately 5% to 75% of the total projected phase diagram area, and said second phase behavior of one of said solvent components produces said bisphenol-A region having an area in the range of approximately 60% to 95% of the total projected phase diagram area.

10. The method of claim 5 wherein the total projected phase diagram area is 0.5 (wt. fraction)$^2$.

11. The method of claim 5 where said first solvent component is acetone, and said second solvent component is water.

12. A method of producing bisphenol-A by crystallization, comprising the following steps:
    reacting phenol and acetone in the presence of a catalyst to form a product solution including bisphenol-A, phenol and solvent, where the bisphenol-A, phenol and solvent exhibit a phase equilibrium relationship represented by a projection of a polythermal ternary phase diagram;
    providing two or more solvent components in said product solution, where one of said solvent components exhibits a first phase behavior and the other of said solvent components exhibits a second phase behavior, where the total solvent concentration is at or below about 40 weight percent; and
    adjusting the concentration ratio of the solvent components in the product solution to control the phase behavior of the product solution to selectively form substantially pure solid bisphenol-A from said product solution during crystallization, where the final separation of substantially pure bisphenol-A is achieved by direct crystallization.

13. The method of claim 12 where the two or more solvent components are comprised of any one or more of the reactants and/or products formed from the reaction.

14. The method of claim 12 further comprising passing the product solution though a single crystallizer and forming substantially pure solid bisphenol-A.

15. The method of claim 12 wherein said first and second phase behaviors are diverse.

16. The method of claim 12 wherein said first and second phase behaviors are similar.

17. A method for producing bisphenol-A from a product solution comprising the following steps:
    forming a product solution comprised of phenol, bisphenol-A, isomers of bisphenol-A, un-reacted reactants and a solvent comprised of two or more solvent components;
    selectively controlling the amount of said solvent in the product solution to manipulate the phase behavior of the product solution such that substantially pure crystalline bisphenol-A/phenol adduct can be crystallized from said product solution, where the total weight percent of solvent prior to crystallization is at or below about 18%;
    separating substantially pure adduct form the product solution by direct crystallization;
    adding solvent comprised of two or more solvent components to the adduct to form an adduct solution, where the total weight percent of solvent prior to crystallization is at or below about 22%;
    selectively controlling the amount of said solvent in the adduct solution to manipulate the phase behavior of the adduct solution such that substantially pure bisphenol-A can be crystallized from said adduct solution,
    separating substantially pure bisphenol-A from the adduct solution by direct crystallization.

18. The method of claim 1 employing two solvent components in a concentration ratio of 80:20 to 20:80, where the first solvent component is water and the second solvent component is acetone.

19. The method of claim 5 employing two solvent components in a concentration ratio of 80:20 to 20:80, where the first solvent component is water and the second solvent component is acetone.

20. The method of claim 12 employing two solvent components in a concentration ratio of 80:20 to 20:80, where the first solvent component is water and the second solvent component is acetone.

21. The method of claim 17 employing two solvent components in a concentration ratio of 80:20 to 20:80, where the first solvent component is water and the second solvent component is acetone.

* * * * *